US012347550B2

(12) United States Patent
Palmer et al.

(10) Patent No.: US 12,347,550 B2
(45) Date of Patent: *Jul. 1, 2025

(54) IMAGING DISCOVERY UTILITY FOR AUGMENTING CLINICAL IMAGE MANAGEMENT

(71) Applicant: Medtronic, Inc., Minneapolis, MN (US)

(72) Inventors: Mark Palmer, Oak Grove, MN (US); Kalvin Parman, Maple Grove, MN (US); Ryan P. Lahm, Lino Lakes, MN (US); Megan Samec, Little Canada, MN (US); Srinivasan S. Varahoor, Windsor, CA (US); Priya Nair, Hayward, CA (US); Julianne Spencer, New Brighton, MN (US); Walton W. Baxter, San Clemente, CA (US); Callie Cronin Myers, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/480,392

(22) Filed: Oct. 3, 2023

(65) Prior Publication Data
US 2024/0029865 A1    Jan. 25, 2024

Related U.S. Application Data

(63) Continuation of application No. 17/349,361, filed on Jun. 16, 2021, now Pat. No. 11,817,201.
(Continued)

(51) Int. Cl.
*G06F 16/22* (2019.01)
*G16H 30/20* (2018.01)
*G16H 30/40* (2018.01)

(52) U.S. Cl.
CPC .......... *G16H 30/20* (2018.01); *G06F 16/221* (2019.01); *G16H 30/40* (2018.01)

(58) Field of Classification Search
CPC ...... G06F 16/50; G06F 16/5866; G06F 16/58; G06F 16/51
See application file for complete search history.

(56) References Cited

U.S. PATENT DOCUMENTS 7,187,964 B2    3/2007   Khoury
7,892,165 B2    2/2011   Nakamura
(Continued)

FOREIGN PATENT DOCUMENTS

CN    107077511 A  *  8/2017  ............. G06F 16/21
CN    107515867 A  *  12/2017 ............. G06F 16/22
(Continued)

OTHER PUBLICATIONS

Costa et al., "Medical imaging archiving: A comparison between several NoSQL solutions", Jun. 2014 IEEE-EMBS International Conference on Biomedical and Health Informatics (BHI), (Year: 2014).*
(Continued)

*Primary Examiner* — Boris Gorney
*Assistant Examiner* — Robert F May
(74) *Attorney, Agent, or Firm* — Michael Best & Friedrich LLP

(57) ABSTRACT

Novel tools and techniques are provided for implementing an imaging discovery utility for augmenting clinical image management. In some embodiments, in response to receiving a request for a first medical image file(s) from a requesting device, a non-relational ("NoSQL") data management system ("DMS") may access a NoSQL database containing, inter alia, a plurality of medical image files that are mirrored copies of a plurality of medical image files
(Continued)

US 12,347,550 B2
Page 2 stored in a relational ("SQL") database, the medical image files each being organized in an image-centric hierarchy with image data being at a top level and patient information associated with the image data being at a lower level. Based on a successful search of the NoSQL database based on search terms in the request, the NoSQL DMS may identify a corresponding second medical image(s) in the SQL database, and may retrieve and send (to the requesting device) the identified second medical image(s).

20 Claims, 22 Drawing Sheets

Related U.S. Application Data

(60) Provisional application No. 63/075,413, filed on Sep. 8, 2020.

(56) References Cited

U.S. PATENT DOCUMENTS

| | | | |
|---|---|---|---|
| 7,998,095 B2 | 8/2011 | McAuley | |
| 8,460,282 B2 | 6/2013 | McAuley | |
| 8,482,859 B2 | 7/2013 | Border et al. | |
| 8,768,022 B2 | 7/2014 | Miga et al. | |
| 8,792,693 B2 | 7/2014 | Satish et al. | |
| 8,902,254 B1 | 12/2014 | Laughlin et al. | |
| 9,128,281 B2 | 9/2015 | Osterhout et al. | |
| 9,134,534 B2 | 9/2015 | Border et al. | |
| 9,223,134 B2 | 12/2015 | Miller et al. | |
| 9,232,982 B2 | 1/2016 | Soler et al. | |
| 9,298,884 B1 | 3/2016 | Ahmad | |
| 9,317,743 B2 | 4/2016 | Datta et al. | |
| 9,452,294 B2 | 9/2016 | Kaula et al. | |
| 9,492,241 B2 | 11/2016 | Joskowicz et al. | |
| 9,526,443 B1 | 12/2016 | Berme et al. | |
| 9,615,788 B2 | 4/2017 | Kaula et al. | |
| 9,639,953 B2 | 5/2017 | Moraviec | |
| 9,642,606 B2 | 5/2017 | Charles et al. | |
| 9,659,104 B2 | 5/2017 | Soon-Shiong et al. | |
| 9,687,301 B2 | 6/2017 | Lee et al. | |
| 9,720,505 B2 | 8/2017 | Gribetz et al. | |
| 9,740,296 B2 | 8/2017 | Cohen et al. | |
| 9,767,608 B2 | 9/2017 | Lee et al. | |
| 9,773,312 B2 | 9/2017 | Lee | |
| 9,855,103 B2 | 1/2018 | Tsekos et al. | |
| 9,866,767 B2 | 1/2018 | Jones | |
| 9,870,060 B2 | 1/2018 | Marggraff et al. | |
| 9,875,540 B2 | 1/2018 | Blumhofer et al. | |
| 9,888,973 B2 | 2/2018 | Olson et al. | |
| 9,911,225 B2 | 3/2018 | Engel et al. | |
| 9,928,588 B2 | 3/2018 | Vilsmeier | |
| 9,947,104 B2 | 4/2018 | Seiler et al. | |
| 9,986,983 B2 | 6/2018 | Weingarten et al. | |
| 10,026,227 B2 | 7/2018 | Laughlin et al. | |
| 10,152,796 B2 | 12/2018 | Guo et al. | |
| 10,180,572 B2 | 1/2019 | Osterhout et al. | |
| 2002/0198891 A1 | 12/2002 | Li et al. | |
| 2007/0173861 A1 | 7/2007 | Strommer et al. | |
| 2008/0033527 A1 | 2/2008 | Nunez et al. | |
| 2010/0198346 A1 | 8/2010 | Keogh et al. | |
| 2012/0188352 A1 | 7/2012 | Wittenberg et al. | |
| 2013/0035757 A1 | 2/2013 | Zentgraf et al. | |
| 2013/0117273 A1* | 5/2013 | Lee | G06F 16/22 707/E17.083 |
| 2013/0339366 A1* | 12/2013 | Khimich | G06F 16/215 707/741 |
| 2014/0128726 A1 | 5/2014 | Quill et al. | |
| 2014/0176661 A1 | 6/2014 | Smurro et al. | |
| 2014/0279881 A1* | 9/2014 | Tan | G06F 16/23 707/613 |
| 2014/0296704 A1 | 10/2014 | Alves De Inda et al. | |
| 2015/0142783 A1* | 5/2015 | Bruce | G06F 16/284 707/722 |
| 2016/0019716 A1 | 1/2016 | Huang et al. | |
| 2016/0085774 A1 | 3/2016 | Bhamidipati et al. | |
| 2016/0350303 A1 | 12/2016 | Fischer et al. | |
| 2017/0021132 A1 | 2/2017 | Zentgraf et al. | |
| 2017/0098333 A1 | 4/2017 | Varga | |
| 2017/0103581 A1 | 4/2017 | Mullins et al. | |
| 2017/0109484 A1 | 4/2017 | Herger et al. | |
| 2017/0206419 A1 | 7/2017 | Mullins | |
| 2017/0221387 A1 | 8/2017 | Lampotang et al. | |
| 2017/0258585 A1 | 9/2017 | Marquez et al. | |
| 2017/0293805 A1 | 10/2017 | Kontschieder et al. | |
| 2017/0295236 A1* | 10/2017 | Kulkarni | H04L 67/1097 |
| 2017/0323148 A1 | 11/2017 | Sarkar et al. | |
| 2017/0340396 A1 | 11/2017 | Romo et al. | |
| 2018/0012416 A1 | 1/2018 | Jones et al. | |
| 2019/0183576 A1 | 6/2019 | Fahim et al. | |
| 2019/0188309 A1* | 6/2019 | Anderson | G06F 3/065 |
| 2019/0298450 A1 | 10/2019 | Dasi et al. | |
| 2019/0350671 A1 | 11/2019 | Varshney et al. | |
| 2019/0362556 A1 | 11/2019 | Ben-Dor et al. | |
| 2019/0384764 A1 | 12/2019 | Taylor | |
| 2020/0060765 A1 | 2/2020 | Fahim et al. | |
| 2020/0129136 A1 | 4/2020 | Harding et al. | |
| 2021/0369393 A1 | 12/2021 | Braido et al. | |
| 2021/0369394 A1 | 12/2021 | Braido et al. | |

FOREIGN PATENT DOCUMENTS

| | | | | |
|---|---|---|---|---|
| CN | 108009296 A | * | 5/2018 | ......... G06F 16/2433 |
| CN | 108984598 A | * | 12/2018 | |
| CN | 111739613 A | * | 10/2020 | ........... G06F 16/182 |
| KR | 101715019 B1 | * | 3/2017 | |
| TR | 201720331 A2 | * | 4/2018 | |
| WO | 2001020552 A1 | | 3/2001 | |
| WO | 2009148317 A1 | | 12/2009 | |
| WO | 2021243310 A1 | | 12/2021 | |
| WO | 2021243311 A1 | | 12/2021 | |
| WO | 2021243313 A1 | | 12/2021 | |
| WO | 2021243314 A1 | | 12/2021 | |
| WO | 2022055588 A1 | | 3/2022 | |

OTHER PUBLICATIONS

International Search Report & Written Opinion, International Application No. PCT/US2021/035033 dated Sep. 14, 2021 (16 pages).
International Search Report & Written Opinion, International Application No. PCT/US2021/035034 dated Sep. 16, 2021 (16 pages).
Zhang Q et al: "Dynamic real-time 4D cardiac MDCT image display using GPU-accelerated volume rendering", Computerized Medical Imaging and Graphics, Pergamon Press, New York, NY, US, vol. 33, No. 6, Sep. 1, 2009, 16 pages.
Azizian Mahdi et al: "Intraoperative 3D stereo visualization for image-guided cardiac ablation", Medical Imaging 2011: Visualization, Image-Guided Procedures, and Modeling, Spie, vol. 7964, No. 1, Mar. 2, 2011, 8 pages.
Linte CA et al: "Virtual and Augmented Medical Imaging Environments: Enabling Technology for Minimally Invasive Cardiac Interventional Guidance", IEEE Reviews in Biomedical Engineering, IEEE, USA, vol. 3, Jan. 1, 2010, 23 pages.
Robb A. Using patient specific anatomic models, IEEE Engineering in Medicine and Biology Magazine, IEEE Service Center, Pisacataway, NJ, US, vol. 15, No. 2, Mar. 1, 1996, 10 pages.
International Search Report & Written Opinion, International Application No. PCT/US2021/035036 dated Septmember 16, 2021 (16 pages).
International Search Report & Written Opinion, International Application No. PCT/US2021/035037 dated Sep. 16, 2021 (16 pages).
Suematsu et al., "Robotic-assisted closure of atrial septal defect under real-time three-dimensional echo guide in vitro study", CP Journal of cardio-Thoracic Surgery, vol. 32, No. 4, dated Sep. 6, 2007, 4 pages.
International Search Report & Written Opinion, International Application No. PCT/US2021/037655 dated Oct. 4, 2021 (19 pages).
Silva et al. "Medical Imaging archiving: A comparison between several NoSQL solutions." IEEE EMBS International Conference

(56) References Cited

OTHER PUBLICATIONS on Information Technology Applications in Biomedicine (ITAB) [online], 2014 [Retrieved on Aug. 12, 2021], Retrieved from the Internet: <URL: https://doi.org/10.1109/BHI.2014.6864305>, see entire document, especially p. 65, Abstract; p. 66, col. 1, para 2-4, 5 pages.

Costa et al., "Medical imaging archiving: A comparison between several NoSQL solutions", IEEE-EMBS International Conference on Biomedical and Health Informatics (BHI), Jun. 2014.

\* cited by examiner

| | | |
|---|---|---|
| Instructions | | |
| Step 1: | Prepare your assets within the required file structure (please point to a supporting document here). | |
| Step 2: | Please add the assets to the data library below with a supporting description. | |
| Step 3: | Complete all required and flexible metadata points within the spreadsheet. | |
| Step 4: | Please include any supporting file structures. | |
| | Data Library | |
| Required Data Point | | |
| Group Specific Optional Data Point | | |
| | | |
| Metadata Label | Definition | Data Type |
| | Source Library | |
| Source Identifier | Source from which the asset is received | Text |
| Study Code | Reason for which the asset was collected | Text |
| Study Description | Description of reason for which the asset was collected | Text |
| Source Institution City | City where the source institution is geographically located | Text |
| Source Geography | Geographic location of the source institution | Text |
| | Subject Library | |
| Study Code | Reason for which the asset was collected | Text |
| Subject ID | Identifier for scan subject | Text |
| Species | Species of scan subject | Text |
| Gender | Gender of scan subject | Text Option |
| YOB | 4 digit year of birth for scan subject | Number |
| Race | Race of scan subject | Text |
| | Scan Library | |
| Subject ID | Identifier for scan subject | Text |
| Scan ID | Identifier for scan asset | Text |
| Scan Date | Date scan was collected (mm/dd/yyyy) | Date |
| Primary Anatomy Subject to... | Primary anatomy depicted in the scan | Text |
| Expected Number of Phases | Number of phases expected/known to be reflected in the scan | Number |

Instructions & Data Library | Source Data | Subject Data | Scan Data | Device Data | Disease Data

| Scan Library | | |
|---|---|---|
| Subject ID | Identifier for scan subject | Text |
| Scan ID | Identifier for scan asset | Text |
| Scan Date | Date scan was collected (mm/dd/yyyy) | Date |
| Primary Anatomical Structure | Primary anatomy depicted in the scan | Text |
| Expected Number of Phases | Number of phases expected/known to be reflected in the scan | Number |
| Subject Weight (lbs) | Weight of scan subject in pounds at time of scan Only need to provide lbs or kg, not both | Measurement |
| Subject Weight (kg) | Weight of scan subject in kilograms at time of scan Only need to provide lbs or kg, not both | Measurement |
| Subject Height (inches) | Height of scan subject in inches at time of scan Only need to provide inches or cm, not both | Measurement |
| Subject Height (cm) | Height of scan subject in centimeters at time of scan Only need to provide inches or cm, not both | Measurement |
| Subject BMI (calculated) | BMI of subject at time of scan | Measurement |
| Subject Scan Age | Age of subject at time of scan | Number |
| Contrast | Y / N presence of contrast in scan | Text Option |
| Quality | High / Low / Medium quality classification of scan | Text Option |
| Subject Healthy | Is patient considered healthy at time of scan? Y/N Option | Text Option |
| Subject NYHA Classification | NYHA classification of subject at time of scan | Text Option |
| Secondary Anatomical Structure(s) | Comma separated list of secondary anatomies depicted in the scan (can add multiple values within a single cell) | Text List |
| Cardiac Cycle Phase | Ex: 10, 20, 30, multiphase | Text |
| Gated / Ungated | Was a cardiac gated scan collection used? | Text Option |
| Comments | Open field comments from researchers | Text |
| Operative Interval | Post operative followup timepoint | Text |
| Indication | Reason scan was collected | Text |
| LVEF (percent) | Left ventricular ejection fraction value (Percent) NOTE: Must be a distinct value; ranges must be calculated to an average | Measurement |
| LVEF Collection Modality | Left ventricular ejection fraction modality (Echo, Ultrasound, ...) | Text Option |
| LVEDD (mm) | Left ventricular diastolic diameter (mm) | Measurement |
| Chest Circumference (in) | Circumference around the chest (in) | Measurement |
| Chest Circumference (cm) | Circumference around the chest (cm) | Measurement |
| | This data will be mined from the DICOM header, unless overwritten in this spreadsheet as an optional data point | Measurement |

| Scan Library | | |
|---|---|---|
| Scan ID | Identifier for scan subject | Text |
| Scan ID | Identifier for scan asset | Text |
| Scan Date | Date scan was collected (mm/dd/yyyy) | Date |
| Primary Anatomical Structure | Primary anatomy depicted in the scan | Text |
| Expected Phases of Cardiac | Number of phases expected/known to be reflected in the scan | Number |
| Subject Weight (lbs) | Weight of scan subject in pounds at time of scan Only need to provide lbs or kg, not both | Measurement |
| Subject Weight (kg) | Weight of scan subject in kilograms at time of scan Only need to provide lbs or kg, not both | Measurement |
| Subject Height (inches) | Height of scan subject in inches at time of scan Only need to provide inches or cm, not both | Measurement |
| Subject Height (cm) | Height of scan subject in centimeters at time of scan Only need to provide inches or cm, not both | Measurement |
| Subject BMI (calculated) | BMI of subject at time of scan | Measurement |
| Subject Scan Age | Age of subject at time of scan | Number |
| Contrast | Y / N presence of contrast in scan | Text Option |
| Quality | High / Low / Medium quality classification of scan | Text Option |
| Subject NYHA Classification | NYHA classification of subject at time of scan | Text Option |
| Secondary Anatomical Structure(s) | Comma separated list of secondary anatomies depicted in the scan (can add multiple values within a single cell) | Text List |
| Cardiac Cycle Phase | Ex: 10, 20, 30 | Text |
| Gated / Ungated | Was a cardiac gated scan collection used? | Text Option |
| Comments | Open field comments from researchers | Text |
| Operative Interval | Post operative followup timepoint | Text |
| Indication | Reason scan was collected | Text |
| LVEF (percent) | Left ventricular ejection fraction value (Percent) | Measurement |
| LVEF Collection Modality | Left ventricular ejection fraction modality (Echo, Ultrasound, | Text Option |
| LVEDD (mm) | Left ventricular diastolic diameter (mm) | Measurement |
| Aortic valve peak gradient (mmHg) | Peak pressure gradient across aortic valve | Measurement |
| Aortic valve mean gradient (mmHg) | Mean pressure gradient across aortic valve | Measurement |
| Aortic valve peak velocity (m/s) | Aortic jet velocity (m/s) | Measurement |
| Aortic valve area (cm^2) | Aortic valve area (cm^2) | Measurement |
| Aortic regurgitation | Amount of aortic regurgitation | Text |
| Mitral valve peak gradient (mmHg) | Peak pressure gradient across mitral valve | Measurement |
| Mitral valve mean gradient (mmHg) | Mean pressure gradient across mitral valve | Measurement |
| Mitral valve peak velocity (m/s) | Mitral jet velocity (m/s) | Measurement |
| Mitral valve area (cm^2) | Mitral valve area (cm^2) | Measurement |
| Mitral regurgitation | Amount of mitral regurgitation | Text |
| Pulmonary valve peak gradient (mm | Peak pressure gradient across pulmonary valve | Measurement |
| Pulmonary valve mean gradient (mm | Mean pressure gradient across pulmonary valve | Measurement |
| Pulmonary valve peak velocity (m/s) | Pulmonary jet velocity (m/s) | Measurement |
| Pulmonary valve area (cm^2) | Pulmonary valve area (cm^2) | Measurement |
| Pulmonary regurgitation | Amount of pulmonic regurgitation | Text |
| Tricuspid valve peak gradient (mmH | Peak pressure gradient across tricuspid valve | Measurement |
| Tricuspid valve mean gradient (mml | Mean pressure gradient across tricuspid valve | Measurement |
| Tricuspid valve peak velocity (m/s) | Tricuspid jet velocity (m/s) | Measurement |
| Tricuspid valve area (cm^2) | Tricuspid valve area (cm^2) | Measurement |
| Tricuspid regurgitation | Amount of tricuspid regurgitation | Text |

Fig. 3C

| Scan Library | | |
|---|---|---|
| Subject ID | Identifier for scan subject | Text |
| Scan ID | Identifier for scan asset | Text |
| Scan Date | Date scan was collected (mm/dd/yyyy) | Date |
| Primary Anatomy of Structure | Primary anatomy depicted in the scan | Text |
| Expected Number of Phases | Number of phases expected/known to be reflected in the scan | Number |
| Subject Weight (lbs) | Weight of scan subject in pounds at time of scan Only need to provide lbs or kg, not both | Measurement |
| Subject Weight (kg) | Weight of scan subject in kilograms at time of scan Only need to provide lbs or kg, not both | Measurement |
| Subject Height (inches) | Height of scan subject in inches at time of scan Only need to provide inches or cm, not both | Measurement |
| Subject Height (cm) | Height of scan subject in centimeters at time of scan Only need to provide inches or cm, not both | Measurement |
| Subject BMI (calculated) | BMI of subject at time of scan | Measurement |
| Subject Scan Age | Age of subject at time of scan | Number |
| Contrast | Y / N presence of contrast in scan | Text Option |
| Quality | High / Low / Medium quality classification of scan | Text Option |
| Subject Healthy | Is patient considered healthy at time of scan? Y/N Option | Text Option |
| | This data will be mined from the DICOM header, unless overwritten in this spreadsheet as an optional data point | Measurement |
| | This data will be mined from the DICOM header, unless overwritten in this spreadsheet as an optional data point | Measurement |
| | This data will be mined from the DICOM header, unless overwritten in this spreadsheet as an optional data point | Measurement |
| | This data will be mined from the DICOM header, unless overwritten in this spreadsheet as an optional data point | Text Option |
| | This data will be mined from the DICOM header, unless overwritten in this spreadsheet as an optional data point | Number |
| | This data will be mined from the DICOM header, unless overwritten in this spreadsheet as an optional data point | Number |
| | This data will be mined from the DICOM header, unless overwritten in this spreadsheet as an optional data point | Text |
| | This data will be mined from the DICOM header, unless overwritten in this spreadsheet as an optional data point | Number |
| Device Library | | |
| Subject ID | Identifier for scan subject | Text |
| Scan ID | Identifier for scan asset | Text |

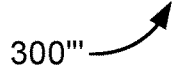

Search the Repository

Search Focus Assets

Diseases
enter disease name

Devices
enter device type

Anatomical Regions
enter anatomical region

Additional Parameters
st

- Source Study Description
- Project Start Date
- Secondary Anatomical Structure(s)
- Source Study / Trial
- Source Study Id
- Source Study Date
- Clinical Trial Study Center

*...ce, Source Study, Modality*

Clear All                                         Search

Manage Searches                    Manage Saved Searches

*Asset // 77 results*                   *Last Run on 2020-Aug-23*

Sources: 1
Subjects: 38
Modalities: 1

Export Results

Save Search

Add to Project

| | Asset Detail ⇕ SORT BY | Subject ID ⇕ | Asset Source ⇕ | Scan Year ⇕ | Baseline Translations ⇕ |
|---|---|---|---|---|---|
| ☐ | CT – Thorax<br>20 Phases, 184 frames /<br>0.40 × 0.40 × 1 | H1643 | Center 1 | 2019 | 0 |
| ☐ | CT – Thorax<br>20 Phases, 246 frames /<br>0.43 × 0.43 × 1 | H1644 | Center 1 | 2019 | 0 |
| ☐ | CT – Thorax<br>20 Phases, 213 frames /<br>0.47 × 0.47 × 1 | H1645 | Center 1 | 2019 | 0 |
| ☐ | CT – Thorax<br>20 Phases, 183 frames /<br>0.42 × 0.42 × 1 | H1646 | Center 1 | 2019 | 0 |
| ☐ | CT – Thorax<br>20 Phases, 191 frames /<br>0.41 × 0.41 × 1 | H1647 | Center 1 | 2019 | 0 |
| ☐ | CT – Thorax<br>20 Phases, 179 frames /<br>0.38 × 0.38 × 1 | H1648 | Center 1 | 2020 | 0 |
| ☐ | CT – Thorax<br>20 Phases, 191 frames /<br>0.44 × 0.44 × 1 | H1649 | Center 1 | 2020 | 0 |
| ☐ | CT – Thorax<br>19 Phases, 207 frames /<br>0.36 × 0.36 × 1 | H1650 | Center 1 | 2020 | 0 |

ASSETS (38) | PROJECTS (0) | SUBJECTS

Scan 1923
CT – Torso
2020-03-29

| Weight | Height | BMI |
|---|---|---|
| 165.72 lbs | 5'11" | 23.1 |

| Scan Age |
|---|
| 34 |

| NYHA |
|---|
| --- |

Subject IU_Code_0697

Species: Human
Sex: Male
YOB: ---
Race: Caucasian

Study
IU_CT_Torso_FY20Q1

Institution
Center 2

Division
Core Test Group

Known Diseases                    0

NO KNOWN DISEASES

Scanned Devices                    0

NO SCANNED DEVICES

Fig. 4D

Scan 314
CT – Pig
2019-12-31

| Weight | Height | BMI |
|---|---|---|
| 154 lbs | --- | --- |

| Scan Age |
|---|
| 17 wks |

Subject Pig_168470

Species: Pig
Sex: Male
YOB: ---
Race: Yorkshire

NYHA
---

Study
Pig

Institution
Center 3

Division
Core Test Group

Known Diseases         0

NO KNOWN DISEASES

Scanned Devices         0

NO SCANNED DEVICES

Search Results

Search Focus: Assets

Diseases
enter disease name

Devices
enter device type

Anatomical Regions
enter anatomical region

Additional Parameters

✗ Source Study / Trial — enter value to search for
✗ Pig what parameter do you want to search?

*Examples: Subject Scan Age, Chest Circumference, Source Study, Modality*

Clear All — Search

Sources: 1
Subjects: 79
Modalities: 1

Export Results
Save Search
Add to Project

Fig. 4K
400

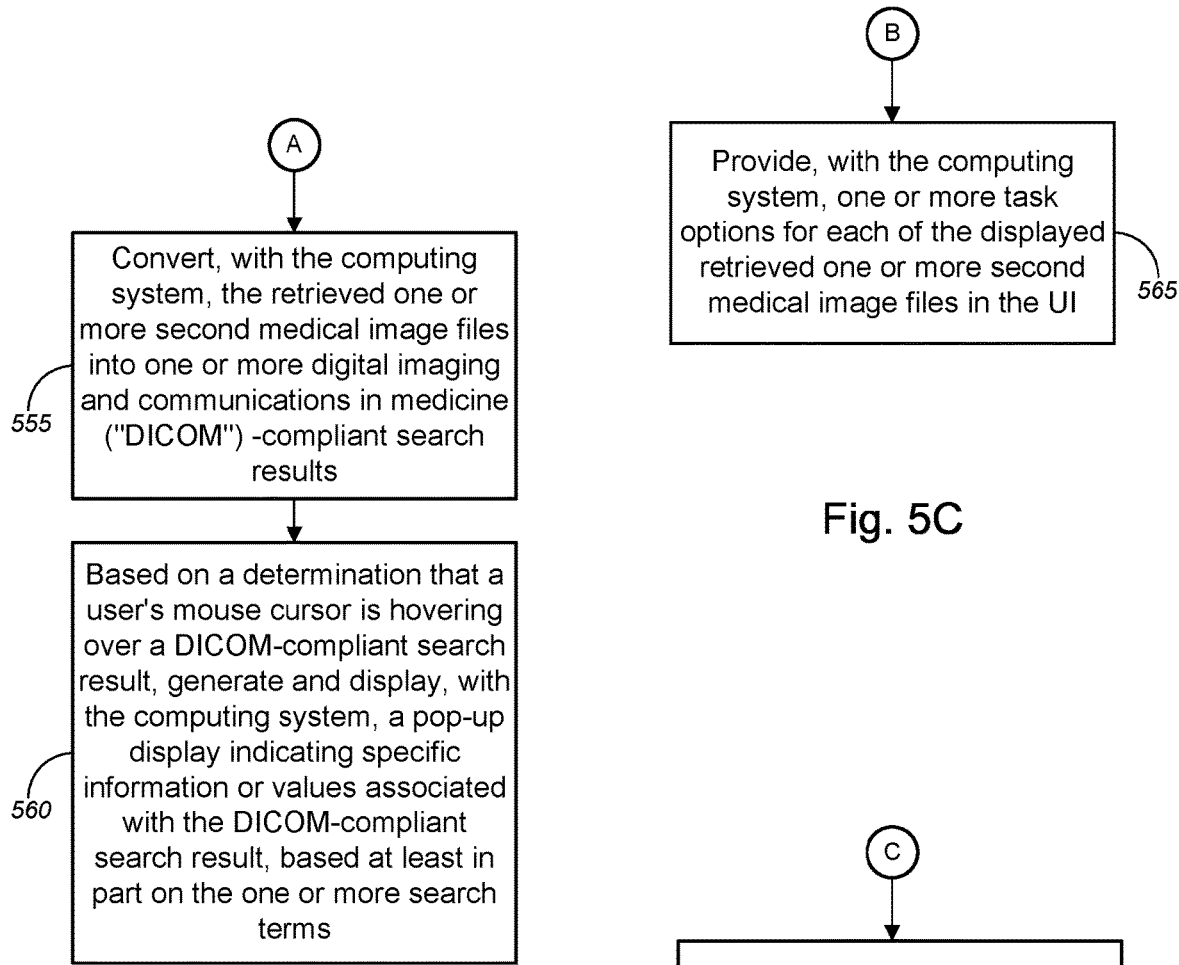
Fig. 5B
Fig. 5C
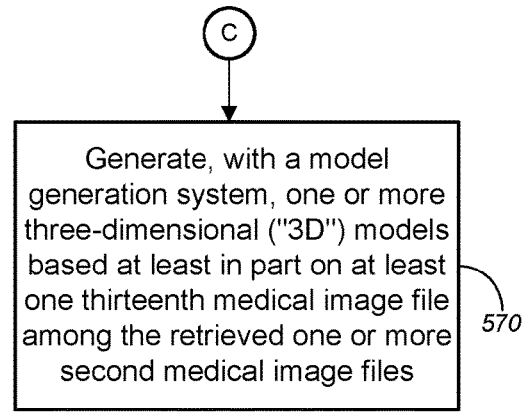
Fig. 5D

IMAGING DISCOVERY UTILITY FOR AUGMENTING CLINICAL IMAGE MANAGEMENT

CROSS-REFERENCE TO RELATED APPLICATIONS

This application is a continuation application of U.S. patent application Ser. No. 17/349,361, filed Jun. 16, 2021, which claims priority to U.S. Patent Application No. 63/075,413, filed Sep. 8, 2020, entitled, "Imaging Discovery Utility for Augmenting Clinical Image Management," the contents of each of which are incorporated herein by reference in their entirety for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to methods, systems, and apparatuses for implementing image management, and, more particularly, to methods, systems, and apparatuses for implementing an imaging discovery utility for augmenting clinical image management.

BACKGROUND

Clinical imaging represents approximately 80% of all clinical data collected in the United States. Conventional commercial clinical image management systems typically focus on secure patient-at-a-time access through specific record identifiers. The metadata regarding what is contained in the image system is stored in a separate repository such as an electronic health record or other database, with no direct link to the image. Some conventional systems also attach artifacts (or artifact files) as an embedded list, which makes it problematic to navigate through the attachments. Such implementations make it difficult (if not impossible) to label, mine, and associate derived artifacts (or artifact files) with the images.

Hence, there is a need for more robust and scalable solutions for implementing image management, and, more particularly, to methods, systems, and apparatuses for implementing an imaging discovery utility for augmenting clinical image management.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

FIGS. 3A-3D are schematic diagrams illustrating various non-limiting examples of image data library metadata that may be used when implementing an imaging discovery utility for augmenting clinical image management, in accordance with various embodiments.

FIGS. 4A-4L are schematic diagrams illustrating various non-limiting examples of user interfaces that may be used when implementing an imaging discovery utility for augmenting clinical image management, in accordance with various embodiments.

FIGS. 5A-5D are flow diagrams illustrating a method for implementing an imaging discovery utility for augmenting clinical image management, in accordance with various embodiments.

DETAILED DESCRIPTION OF CERTAIN EMBODIMENTS

Overview

Figure 1:
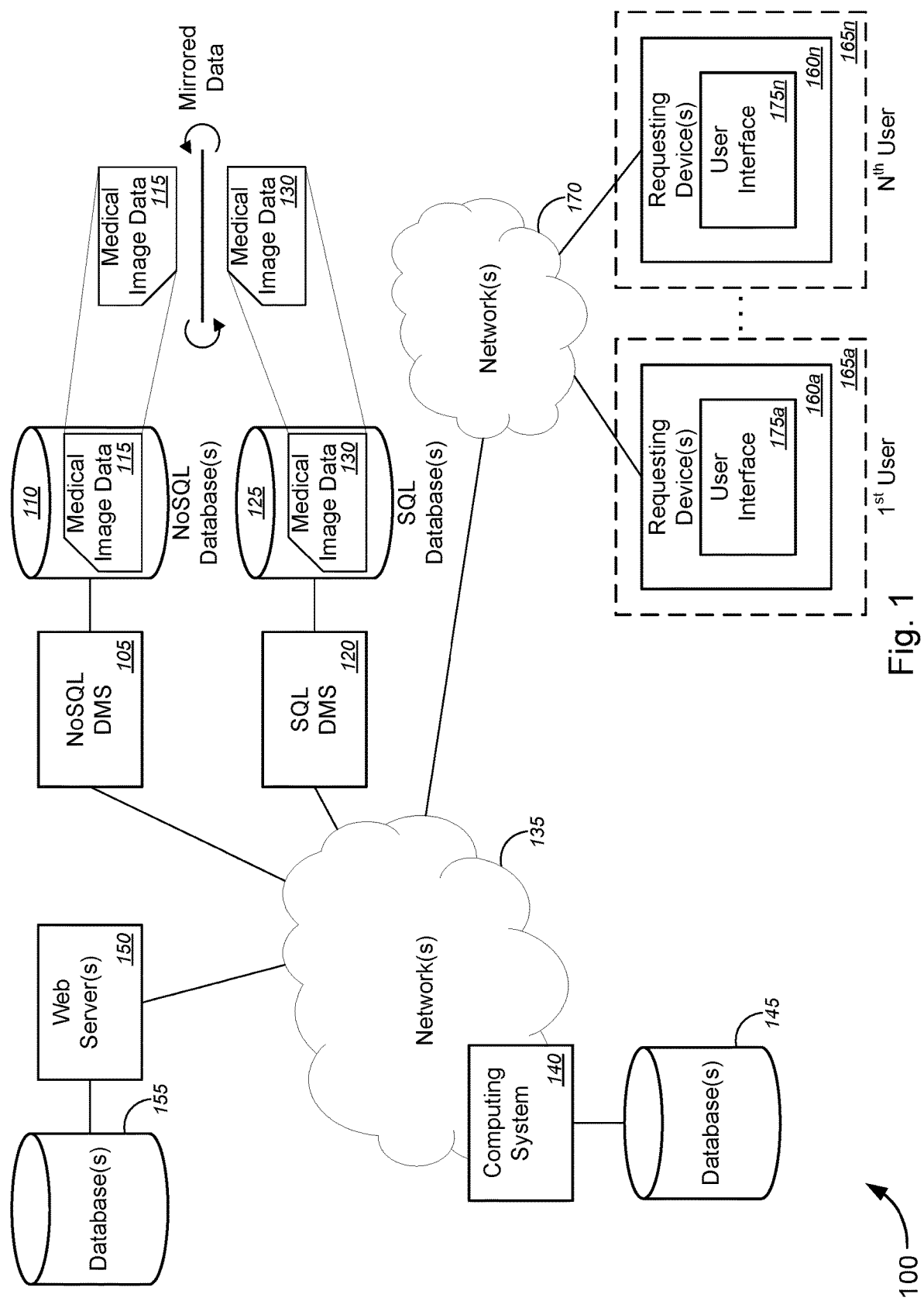
FIG. 1 is a schematic diagram illustrating a system for implementing an imaging discovery utility for augmenting clinical image management, in accordance with various embodiments.

Various embodiments provide tools and techniques for implementing image management, and, more particularly, to methods, systems, and apparatuses for implementing an imaging discovery utility for augmenting clinical image management.

In various embodiments, a non-relational ("NoSQL") data management system ("DMS") might receive, from a requesting device that is associated with a user, a request for at least one first medical image file, the request comprising one or more search terms. In some embodiments, the one or more search terms may include, without limitation, at least one of one or more search criteria, one or more keywords regarding at least one project description, one or more keywords regarding at least one source study name, one or more keywords regarding at least one anatomical region, one or more keywords regarding at least one characteristic of a class of patients, one or more keywords regarding at least one demographic of patients, one or more keywords regarding at least one physical characteristic of patients, one or more keywords regarding at least one characteristic of a disease, one or more keywords regarding at least one characteristic of one or more comorbidities, one or more keywords regarding at least one characteristic of each medical image that satisfies the one or more search criteria, one or more keywords regarding at least one characteristic of at least one modality used to obtain one or more medical images that satisfy the one or more search criteria, one or more keywords regarding at least one characteristic of at least one imaging device used to obtain one or more medical images that satisfy the one or more search criteria, or one or more keywords regarding at least one additional parameter, and/or the like.

The NoSQL DMS might access a NoSQL database that is managed by the NoSQL DMS, and might perform a search of the NoSQL database, by searching for each of the one or more search terms in the plurality of metadata tags associated with each medical image file among the plurality of medical image files in the NoSQL database. Based on a determination that at least one metadata tag associated with one or more second medical image files among the plurality of medical image files contains keywords that correspond to or match at least one search term among the one or more search terms, the NoSQL DMS might identify corresponding one or more second medical image files as stored in a relational ("SQL") database that is managed by a SQL DMS, where the search of the NoSQL database serves as an index search of the SQL database—due to the mirrored data being stored in the NoSQL and SQL databases. At least one of the NoSQL DMS and/or the SQL DMS might retrieve, from the SQL database, the one or more second medical image files, and might send the retrieved one or more second medical image files to the requesting device. In some instances, sending the retrieved one or more second medical image files to the requesting device may, alternatively or additionally, comprise sending, with the at least one of the NoSQL DMS or the SQL DMS, a list of relevant search results to the requesting device, the list of relevant search results comprising the retrieved one or more second medical image files, wherein the retrieved one or more second medical image files may include, but is not limited to, two or more medical image files that are associated with a plurality of different patients.

In some embodiments, a computing system might receive, from the requesting device, the request for the at least one first medical image file, and might query the NoSQL DMS for the requested at least one first medical image file, by relaying the request to the NoSQL DMS. In some cases, the computing system might present a user interface ("UI") via the requesting device. In such cases, the request might be received via the UI. In some instances, sending the retrieved one or more second medical image files to the requesting device may comprise displaying the retrieved one or more second medical image files in the UI.

According to some embodiments, the computing system might convert the retrieved one or more second medical image files into one or more DICOM-compliant search results. In some cases, displaying the retrieved one or more second medical image files in the UI may comprise displaying the retrieved one or more second medical image files as the converted one or more DICOM-compliant search results in the UI. In some instances, based on a determination that a user's mouse cursor is hovering over a DICOM-compliant search result, the computing system might generate and display a pop-up display indicating specific information or values associated with the DICOM-compliant search result, based at least in part on the one or more search terms.

In some embodiments, the computing system might provide one or more task options for each of the displayed retrieved one or more second medical image files in the UI. In some cases, the one or more task options may include, without limitation, at least one of options to download particular one or more third medical image files among the one or more second medical image files, options to add particular one or more fourth medical image files among the one or more second medical image files to at least one project group folder, options to link together at least two fifth medical image files among the one or more second medical image files, options to export one or more sixth medical image files among the one or more second medical image files, options to share one or more seventh medical image files among the one or more second medical image files, options to upload one or more eighth medical image files, options to start a new search, options to save a current search, options to manage saved searches, options to view recent searches, options to export searches, options to open a new project folder, options to save a current project folder, options to manage project folders, options to complete a current project, options to view active projects, or options to export project folders, and/or the like.

According to some embodiments, a model generation system (which, in some cases, may be embodied in the computing system, or the like) might generate one or more three-dimensional ("3D") models based at least in part on at least one twelfth medical image file among the retrieved one or more second medical image files.

In some aspects, based on a determination that contents of one of the NoSQL database that is managed by the NoSQL DMS or the SQL database that is managed by the SQL DMS have changed, the system (i.e., at least one of the NoSQL DMS, the SQL DMS, or the computing system, or the like; also referred to herein as "image discovery utility" or the like) might autonomously mirror the changed contents in the other of the NoSQL database or the SQL database.

Importantly, the imaging discovery utility described with respect to the various embodiments addresses each of the challenges mentioned above with respect to the conventional commercial clinical image management systems (namely, challenges in terms of labelling, mining, and associating derived artifacts or artifact files with the clinical images), by enabling dynamic tagging of imaging records, enabling searching across all images under image management (regardless of which patient the images are associated with), and enabling linking of the images to data and artifacts (or artifact files) derived from the images.

The solution implements the coupling of a structured and unstructured database. The structured database may contain the minimum required data fields to make the image discoverable or searchable, while the unstructured database may provide the capability to dynamically enhance or enrich data fields based on user needs or as more information is derived from the image. The data structure also links artifacts to the image, such artifacts including, but not limited to, image processing analysis files, segmentation files, three-dimensional ("3D") print files, machine learning ("ML") algorithm files, and/or the like. Searches may be performed across the data fields as well as across the associated files and artifacts. An additional feature of the system is the ability to aggregate images into sets or collections based on search criteria. The system is able to search imaging assets and related artifacts, which can be organized in a project collection. The system also allows discoverability and reuse of information and artifacts that are costly to extract from the image. The reuse of imaging provides a larger volume of evidence for research and development applications and/or for regulatory applications, while improving research and development productivity and cost avoidance arising from purchasing duplicate imaging. The system provides a rapid response to regulatory or clinical questions, while providing knowledge capture and sharing across different business units, and provides the ability to identify and strategically fill imaging needs beyond one business unit or company. Applications include creating a focused set of data with a set of common criteria on which to create or apply artificial intelligence ("AI") and/or ML methods, atlas-based segmentation methods, or other types of analytics, or the like.

These and other aspects of the imaging discovery utility for augmenting clinical image management are described in greater detail with respect to the figures.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Various embodiments described herein, while embodying (in some cases) software products, computer-performed methods, and/or computer systems, represent tangible, concrete improvements to existing technological areas, including, without limitation, image management technology, medical image management technology, medical image discovery technology, user interface technology, and/or the like. In other aspects, certain embodiments, can improve the functioning of user equipment or systems themselves (e.g., image management system, medical image management system, medical image discovery system, user interface system, etc.), for example, by receiving, with a non-relational ("NoSQL") data management system ("DMS") and from a requesting device, a request for at least one first medical image file, the request comprising one or more search terms; accessing, with the NoSQL DMS, a NoSQL database that is managed by the NoSQL DMS, the NoSQL database containing a plurality of medical image files, a plurality of metadata tags associated with each medical image file, and a plurality of artifact files associated with two or more of the plurality of medical image files, the NoSQL database containing mirrored copies of the plurality of medical image files that are stored in a relational ("SQL") database that is managed by a SQL DMS, wherein the plurality of medical image files contained in the NoSQL database and in the SQL database are each organized in an image-centric hierarchy with image data being at a top level of the image-centric hierarchy and patient information associated with the image data being at a level below the top level of the image-centric hierarchy; performing, with the NoSQL DMS, a search of the NoSQL database, by searching for each of the one or more search terms in the plurality of metadata tags associated with each medical image file among the plurality of medical image files in the NoSQL database; and based on a determination that at least one metadata tag associated with one or more second medical image files among the plurality of medical image files contains keywords that correspond to or match at least one search term among the one or more search terms: identifying, with the NoSQL DMS, corresponding one or more second medical image files as stored in the SQL database, wherein the search of the NoSQL database serves as an index search of the SQL database; retrieving, with at least one of the NoSQL DMS or the SQL DMS and from the SQL database, the one or more second medical image files; and sending, with the at least one of the NoSQL DMS or the SQL DMS, the retrieved one or more second medical image files to the requesting device; and/or the like.

In particular, to the extent any abstract concepts are present in the various embodiments, those concepts can be implemented as described herein by devices, software, systems, and methods that involve specific novel functionality (e.g., steps or operations), such as, mirroring medical image data in the NoSQL database and SQL database; utilizing the NoSQL DMS and the NoSQL database to perform robust indexing search functions for searching for mirrored medical image data stored in the SQL database; organizing the medical image data in an image-centric hierarchy within the NoSQL database and within the SQL database, with image data being at a top level of the image-centric hierarchy and patient information associated with the image data being at a level below the top level of the image-centric hierarchy; and/or the like, to name a few examples, that extend beyond mere conventional computer processing operations. These functionalities can produce tangible results outside of the implementing computer system, including, merely by way of example, enabling dynamic tagging of imaging records, enabling searching across all images under image management (regardless of which patient the images are associated with), enabling linking of the images to data and artifacts (or artifact files) derived from the images, aggregating images into sets or collections based on search criteria, allowing discoverability and reuse of information and artifacts that are costly to extract from the image, providing a rapid response to regulatory or clinical questions, while providing knowledge capture and sharing across different business units, and providing the ability to identify and strategically fill imaging needs beyond one business unit or company, and/or the like, at least some of which may be observed or measured by users (e.g., healthcare professionals, researchers, etc.) and/or service providers.

In an aspect, a method may comprise receiving, with a non-relational ("NoSQL") data management system ("DMS") and from a requesting device, a request for at least one first medical image file, the request comprising one or more search terms; and accessing, with the NoSQL DMS, a NoSQL database that is managed by the NoSQL DMS, the NoSQL database containing a plurality of medical image files, a plurality of metadata tags associated with each medical image file, and a plurality of artifact files associated with two or more of the plurality of medical image files. The NoSQL database may contain mirrored copies of the plurality of medical image files that are stored in a relational ("SQL") database that is managed by a SQL DMS, wherein the plurality of medical image files contained in the NoSQL database and in the SQL database are each organized in an image-centric hierarchy with image data being at a top level of the image-centric hierarchy and patient information associated with the image data being at a level below the top level of the image-centric hierarchy. The method may also comprise performing, with the NoSQL DMS, a search of the NoSQL database, by searching for each of the one or more search terms in the plurality of metadata tags associated with each medical image file among the plurality of medical image files in the NoSQL database. The method may further comprise, based on a determination that at least one metadata tag associated with one or more second medical image files among the plurality of medical image files contains keywords that correspond to or match at least one search term among the one or more search terms: identifying, with the NoSQL DMS, corresponding one or more second medical image files as stored in the SQL database, wherein the search of the NoSQL database serves as an index search of the SQL database; retrieving, with at least one of the NoSQL DMS or the SQL DMS and from the SQL database, the one or more second medical image files; and sending, with the at least one of the NoSQL DMS or the SQL DMS, the retrieved one or more second medical image files to the requesting device.

In some embodiments, the method may further comprise receiving, with a computing system and from the requesting device, the request for the at least one first medical image file; and querying, with the computing system, the NoSQL DMS for the requested at least one first medical image file, by relaying the request to the NoSQL DMS. In some instances, the method may further comprise presenting, with the computing system, a user interface ("UI") via the requesting device; wherein the request is received via the UI; and wherein sending the retrieved one or more second medical image files to the requesting device may comprise displaying the retrieved one or more second medical image files in the UI. In some cases, the method may further comprise converting, with the computing system, the retrieved one or more second medical image files into one or more digital imaging and communications in medicine ("DICOM")-compliant search results; wherein displaying the retrieved one or more second medical image files in the UI may comprise displaying the retrieved one or more second medical image files as the converted one or more DICOM-compliant search results in the UI. In some instances, the method may further comprise, based on a determination that a user's mouse cursor is hovering over a DICOM-compliant search result, generating and displaying, with the computing system, a pop-up display indicating specific information or values associated with the DICOM-compliant search result, based at least in part on the one or more search terms.

According to some embodiments, the method may further comprise providing, with the computing system, one or more task options for each of the displayed retrieved one or more second medical image files in the UI. In some cases, the one or more task options may comprise at least one of options to download particular one or more third medical image files among the one or more second medical image files, options to add particular one or more fourth medical image files among the one or more second medical image files to at least one project group folder, options to link together at least two fifth medical image files among the one or more second medical image files, options to export one or more sixth medical image files among the one or more second medical image files, options to share one or more seventh medical image files among the one or more second medical image files, options to upload one or more eighth medical image files, options to start a new search, options to save a current search, options to manage saved searches, options to view recent searches, options to export searches, options to open a new project folder, options to save a current project folder, options to manage project folders, options to complete a current project, options to view active projects, or options to export project folders, and/or the like. In some instances, two or more ninth medical image files among the one or more second medical image files that are obtained during a single imaging session may be grouped together as a single imaging asset with at least one of shared metadata, common metadata, or linked metadata, and/or the like. In some cases, the one or more task options may further comprise at least one of options to preview the two or more ninth medical image files together in the UI, options to download the two or more ninth medical image files as a single set of image files, options to export the two or more ninth medical image files as a single set of image files, options to share the two or more ninth medical image files as a single set of image files, or options to edit metadata associated with each of the two or more ninth medical image files individually or as a group, and/or the like. Alternatively, or additionally, the one or more task options may further comprise at least one of options to perform auto-segmentation for one or more tenth medical image files among the one or more second medical image files, or options to perform auto-measurements for one or more eleventh medical image files among the one or more second medical image files, and/or the like.

In some embodiments, the computing system may comprise at least one of a processor of a NoSQL DMS, a processor of a SQL DMS, a processor of a hybrid NoSQL/SQL DMS, a controller for both the NoSQL DMS and the SQL DMS, a server computer over a network, a cloud-based computing system over a network, or a distributed computing system, and/or the like. In some cases, the requesting device may comprise at least one of a laptop computer, a desktop computer, a tablet computer, a smart phone, a mobile phone, or a web client, and/or the like. In some instances, the plurality of artifact files may comprise at least one of one or more raw image data files, one or more document files, one or more image processing analysis files, one or more segmentation files, one or more three-dimensional ("3D") print files, one or more stereolithography ("STL") files, one or more measurement files, one or more experiment files, one or more project files, one or more machine algorithm files, or one or more report files, and/or the like. According to some embodiments, a metadata tag associated with a medical image file among the plurality of medical image files may comprise a link between a metadata attribute associated with the medical image file and one or more artifact files among the plurality of artifact files.

In some instances, performing the search of the NoSQL database may comprise performing metadata search associated with the plurality of medical image files across a plurality of subjects based on attributes of medical image files and without searching based on patient data one subject at a time, each medical image file being defined as a root node of each data structure and each corresponding subject associated with a medical image file being defined as a subordinate node of the data structure. Merely by way of example, in some cases, the one or more search terms may comprise at least one of one or more search criteria, one or more keywords regarding at least one project description, one or more keywords regarding at least one source study name, one or more keywords regarding at least one anatomical region, one or more keywords regarding at least one characteristic of a class of patients, one or more keywords regarding at least one demographic of patients, one or more keywords regarding at least one physical characteristic of patients, one or more keywords regarding at least one characteristic of a disease, one or more keywords regarding at least one characteristic of one or more comorbidities, one or more keywords regarding at least one characteristic of each medical image that satisfies the one or more search criteria, one or more keywords regarding at least one characteristic of at least one modality used to obtain one or more medical images that satisfy the one or more search criteria, one or more keywords regarding at least one characteristic of at least one imaging device used to obtain one or more medical images that satisfy the one or more search criteria, or one or more keywords regarding at least one additional parameter, and/or the like.

According to some embodiments, the plurality of metadata tags may comprise flexible image tagging that is customizable to include one or more standard medical image metadata and one or more non-standard medical image metadata. In some cases, the one or more standard medical image metadata may comprise one or more digital imaging and communications in medicine ("DICOM")-compliant metadata. In some instances, the one or more non-standard medical image metadata may comprise at least one of contrast metadata, metadata associated with device attribute, metadata associated with implant technique, metadata regarding whether patient is healthy or not, metadata regarding quality of scan of image, metadata associated with one or more specific parameters used by at least one medical specialty, one or more group specific metadata, one or more group specific metadata attributes, or one or more customizable metadata, and/or the like.

In some embodiments, sending the retrieved one or more second medical image files to the requesting device may comprise sending, with the at least one of the NoSQL DMS or the SQL DMS, a list of relevant search results to the requesting device, the list of relevant search results comprising the retrieved one or more second medical image files, wherein the retrieved one or more second medical image files may comprise two or more twelfth medical image files that are associated with a plurality of different patients.

According to some embodiments, the method may further comprise generating, with a model generation system, one or more three-dimensional ("3D") models based at least in part on at least one thirteenth medical image file among the retrieved one or more second medical image files.

In another aspect, a system might comprise a relational ("SQL") database that is managed by a SQL data management system ("DMS"); the SQL DMS; a non-relational ("NoSQL") database that is managed by a NoSQL DMS; and the NoSQL DMS. The NoSQL database may contain a plurality of medical image files, a plurality of metadata tags associated with each medical image file, and a plurality of artifact files associated with two or more of the plurality of medical image files, the NoSQL database containing mirrored copies of the plurality of medical image files that are stored in the SQL database that is managed by the SQL DMS, wherein the plurality of medical image files contained in the NoSQL database and in the SQL database are each organized in an image-centric hierarchy with image data being at a top level of the image-centric hierarchy and patient information associated with the image data being at a level below the top level of the image-centric hierarchy;

The NoSQL DMS might comprise at least one first processor and a first non-transitory computer readable medium communicatively coupled to the at least one first processor. The first non-transitory computer readable medium might have stored thereon computer software comprising a first set of instructions that, when executed by the at least one first processor, causes the NoSQL DMS to: receive, from a requesting device, a request for at least one first medical image file, the request comprising one or more search terms; access the NoSQL database that is managed by the NoSQL DMS; perform a search of the NoSQL database, by searching for each of the one or more search terms in the plurality of metadata tags associated with each medical image file among the plurality of medical image files in the NoSQL database; and based on a determination that at least one metadata tag associated with one or more second medical image files among the plurality of medical image files contains keywords that correspond to or match at least one search term among the one or more search terms: identify corresponding one or more second medical image files as stored in the SQL database, wherein the search of the NoSQL database serves as an index search of the SQL database; retrieve, from the SQL database, the one or more second medical image files; and send the retrieved one or more second medical image files to the requesting device.

In some embodiments, the system may further comprise a computing system, comprising: at least one second processor; and a second non-transitory computer readable medium communicatively coupled to the at least one second processor, the second non-transitory computer readable medium having stored thereon computer software comprising a second set of instructions that, when executed by the at least one second processor, causes the computing system to: receive, from the requesting device, the request for the at least one first medical image file; and query the NoSQL DMS for the requested first medical image file, by relaying the request to the NoSQL DMS.

In yet another aspect, a method may comprise, based on a determination that contents of one of a non-relational ("NoSQL") database that is managed by a NoSQL data management system ("DMS") or a relational ("SQL") database that is managed by a SQL DMS have changed, autonomously mirroring the changed contents in the other of the NoSQL database or the SQL database, the NoSQL database containing a plurality of medical image files, a plurality of metadata tags associated with each medical image file, and a plurality of artifact files associated with two or more of the plurality of medical image files, the NoSQL database containing mirrored copies of the plurality of medical image files that are stored in the SQL database, wherein the plurality of medical image files contained in the NoSQL database and in the SQL database are each organized in an image-centric hierarchy with image data being at a top level of the image-centric hierarchy and patient information associated with the image data being at a level below the top level of the image-centric hierarchy.

In still another aspect, a method may comprise receiving, with one of a non-relational ("NoSQL") data management system ("DMS") or a relational ("SQL") DMS and from a user device associated with a user, a request to modify metadata attributes associated with a medical image file that is stored and mirrored in each of a NoSQL database managed by the NoSQL DMS and a SQL database managed by the SQL DMS. The method may also comprise presenting, with the one of the NoSQL DMS or the SQL DMS, a user interface ("UI") with options for the user to dynamically modify metadata attributes associated with the medical image file, wherein the options to dynamically modify metadata attributes comprises at least one of dynamically adding group specific metadata attributes to metadata fields of the medical image file, dynamically modifying group specific metadata attributes in metadata fields of the medical image file, dynamically deleting group specific metadata attributes in metadata fields of the medical image file, dynamically defining new group specific metadata fields of the medical image file, dynamically modifying group specific metadata fields of the medical image file, dynamically deleting group specific metadata fields of the medical image file, or dynamically linking a metadata field with one or more artifact files, and/or the like. The method may further comprise, in response to receiving user input based on the presented options to dynamically modify metadata attributes associated with the medical image file, updating at least one of group specific metadata fields or group specific metadata attributes associated with the medical image file in one of the NoSQL database or the SQL database, and mirroring changes to the at least one of group specific metadata fields or group specific metadata attributes associated with the medical image file in the other of the NoSQL database or the SQL database.

In another aspect, a method may comprise receiving, with one of a non-relational ("NoSQL") data management system ("DMS") or a relational ("SQL") DMS and from a user device associated with a user, a request to associate one or more artifact files with a metadata attribute associated with a medical image file that is stored and mirrored in each of a NoSQL database managed by the NoSQL DMS and a SQL database managed by the SQL DMS. The method may also comprise presenting, with the one of the NoSQL DMS or the SQL DMS, a user interface ("UI") with options for the user to modify the metadata attribute associated with the medical image file to include a link between the metadata attribute with the one or more artifact files. The method may further comprise, in response to receiving user input based on the presented options to modify the metadata attribute associated with the medical image file, updating a metadata field associated with the metadata attribute in one of the NoSQL database or the SQL database to include the link between the metadata attribute with the one or more artifact files, and mirroring changes to at least one of the metadata field or the metadata attribute in the other of the NoSQL database or the SQL database, wherein the link between the metadata attribute with the one or more artifact files comprises a relational map between the metadata attribute and each of the one or more artifact files.

In still another aspect, a method may comprise, in response to receiving a request for at least one first medical image file, performing, with a non-relational ("NoSQL") data management system ("DMS"), an index search of a NoSQL database for medical image files associated with a plurality of subjects, the NoSQL database containing a plurality of medical image files, a plurality of metadata tags associated with each medical image file, and a plurality of artifact files associated with two or more of the plurality of medical image files, the NoSQL database containing mirrored copies of the plurality of medical image files that are stored in a relational ("SQL") database that is managed by a SQL DMS. The method may further comprise retrieving the requested at least one first medical image file from the SQL database, based on the index search of the NoSQL database. In some cases, performing the index search may comprise performing metadata search associated with the plurality of medical image files across the plurality of subjects based on attributes of medical image files and without searching based on patient data one subject at a time, each medical image file being defined as a root node of each data structure and each corresponding subject associated with a medical image file being defined as a subordinate node of the data structure.

Various modifications and additions can be made to the embodiments discussed without departing from the scope of the invention. For example, while the embodiments described above refer to particular features, the scope of this invention also includes embodiments having different combination of features and embodiments that do not include all of the above described features.

Specific Exemplary Embodiments

We now turn to the embodiments as illustrated by the drawings. FIGS. 1-7 illustrate some of the features of the method, system, and apparatus for implementing image management, and, more particularly, to methods, systems, and apparatuses for implementing an imaging discovery utility for augmenting clinical image management, as referred to above. The methods, systems, and apparatuses illustrated by FIGS. 1-7 refer to examples of different embodiments that include various components and steps, which can be considered alternatives or which can be used in conjunction with one another in the various embodiments. The description of the illustrated methods, systems, and apparatuses shown in FIGS. 1-7 is provided for purposes of illustration and should not be considered to limit the scope of the different embodiments.

With reference to the figures, FIG. 1 is a schematic diagram illustrating a system 100 for implementing an imaging discovery utility for augmenting clinical image management, in accordance with various embodiments.

In the non-limiting embodiment of FIG. 1, system 100 may comprise a non-relational ("NoSQL") data management system ("DMS") 105 and corresponding NoSQL database 110. In some embodiments, the NoSQL database 110 may contain medical image data 115, which may include, without limitation, a plurality of medical image files, a plurality of metadata tags associated with each medical image file, and a plurality of artifact files associated with two or more of the plurality of medical image files, and/or the like. System 100 may further comprise a relational ("SQL") DMS 120 and corresponding SQL database 125. According to some embodiments, the SQL database 125 may contain medical image data 130, which may include, without limitation, a plurality of medical image files, a plurality of metadata tags associated with each medical image file, and a plurality of artifact files associated with two or more of the plurality of medical image files, and/or the like. In some instances, the NoSQL database 110 may contain mirrored copies of the plurality of medical image files that are stored in the SQL database 125 that is managed by the SQL DMS 120 (denoted in FIG. 1 by symbols labelled "Mirrored Data"). The plurality of medical image files contained in the NoSQL database 110 and in the SQL database 125 may each be organized in an image-centric hierarchy with image data being at a top level of the image-centric hierarchy and patient information associated with the image data being at a level below the top level of the image-centric hierarchy, which is an improvement in terms of image discover and management over conventional data management systems, which are patient-centric, with the patient information being at a top level of the patient-centric hierarchy and image information associated with the patient data being at a level below the top level of the patient-centric hierarchy.

Herein, structured query language ("SQL") might refer to a standard language that is used for handling relational databases, which define relationships in the form of tables.

On the other hand, NoSQL (which might stand for "not only SQL" or not SQL" or the like) might refer to a non-relational data management system ("DMS"), which uses a dynamic schema (instead of a fixed or predefined schema used by SQL databases), avoids joins, is easy to scale (as NoSQL can utilize common hardware and thus scale by increasing the database servers in a pool of resources to reduce load ("horizontally scalable"), whereas SQL requires specialized database hardware for better performance and thus scale by increasing performance of specialized equipment ("vertically scalable")), and can be at least one of document-based, key-value pair-based, column-based, or graph-based, and/or the like. While traditional relational database management systems use SQL syntax to store and retrieve data, a NoSQL database system encompasses a broad range of database technologies that may be used to store structured, semi-structured, unstructured, and/or polymorphic data.

In some cases, the plurality of artifact files may include, but is not limited to, at least one of one or more raw image data files, one or more document files, one or more image processing analysis files, one or more segmentation files, one or more three-dimensional ("3D") print files, one or more stereolithography ("STL") files, one or more measurement files, one or more experiment files, one or more project files, one or more machine algorithm files, or one or more report files, and/or the like. According to some embodiments, a metadata tag associated with a medical image file among the plurality of medical image files may include a link between a metadata attribute associated with the medical image file and one or more artifact files among the plurality of artifact files. In some instances, the plurality of metadata tags may include, without limitation, flexible image tagging that is customizable to include one or more standard medical image metadata and one or more non-standard medical image metadata. In some cases, the one or more standard medical image metadata may comprise one or more digital imaging and communications in medicine ("DICOM")-compliant metadata. In some instances, the one or more non-standard medical image metadata may include, but are not limited to, at least one of contrast metadata, metadata associated with device attribute, metadata associated with implant technique, metadata regarding whether patient is healthy or not, metadata regarding quality of scan of image, metadata associated with one or more specific parameters used by at least one medical specialty, one or more group specific metadata, one or more group specific metadata attributes, or one or more customizable metadata, and/or the like.

System 100 may further comprise one or more networks 135, a computing system 140 and corresponding database(s) 145, and web server(s) 150 and corresponding database(s) 155, the computing system 140 and the web server(s) 150 may each communicatively couple with the NoSQL DMS 105 and/or the SQL DMS 120 via the one or more networks 135. In some embodiments, the computing system may include, without limitation, at least one of a processor of a NoSQL DMS, a processor of a SQL DMS, a processor of a hybrid NoSQL/SQL DMS, a controller for both the NoSQL DMS and the SQL DMS, a server computer over a network, a cloud-based computing system over a network, or a distributed computing system, and/or the like.

System 100 may further comprise one or more requesting devices 160a-160n (collectively, "requesting devices 160" or the like) associated with first through $N^{th}$ users 165a-165n (collectively, "users 165" or the like), respectively. In some instances, the one or more requesting devices may each include, but is not limited to, at least one of a laptop computer, a desktop computer, a tablet computer, a smart phone, a mobile phone, or a web client, and/or the like. The one or more requesting devices 160 may communicatively couple with at least one of the NoSQL DMS 105, the SQL DMS 120, the computing system 140, and/or the web server(s) 150 via the one or more networks 135 and one or more networks 170. System 100 may further comprise one or more user interfaces ("UIs") 175a-175n (collectively, "UIs 175" or the like), each being displayed in a corresponding requesting device 160 among the one or more requesting devices 160a-160n.

Merely by way of example, network(s) 135 and/or network(s) 170 might each include a local area network ("LAN"), including, without limitation, a fiber network, an Ethernet network, a Token-Ring™ network, and/or the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including, without limitation, a network operating under any of the IEEE 802.11 suite of protocols, the Bluetooth™ protocol known in the art, and/or any other wireless protocol; and/or any combination of these and/or other networks. In a particular embodiment, network(s) 135 and/or network(s) 170 might each include an access network of an Internet service provider ("ISP"). In another embodiment, network(s) 135 and/or network(s) 170 might each include a core network of the ISP, and/or the Internet.

In operation, the NoSQL DMS 105 might receive, from a requesting device 160 that is associated with a user 165 (via networks 135 and 170, or the like), a request for at least one first medical image file, the request comprising one or more search terms. In some embodiments, the one or more search terms may include, without limitation, at least one of one or more search criteria, one or more keywords regarding at least one project description, one or more keywords regarding at least one source study name, one or more keywords regarding at least one anatomical region, one or more keywords regarding at least one characteristic of a class of patients, one or more keywords regarding at least one demographic of patients, one or more keywords regarding at least one physical characteristic of patients, one or more keywords regarding at least one characteristic of a disease, one or more keywords regarding at least one characteristic of one or more comorbidities, one or more keywords regarding at least one characteristic of each medical image that satisfies the one or more search criteria, one or more keywords regarding at least one characteristic of at least one modality used to obtain one or more medical images that satisfy the one or more search criteria, one or more keywords regarding at least one characteristic of at least one imaging device used to obtain one or more medical images that satisfy the one or more search criteria, or one or more keywords regarding at least one additional parameter, and/or the like.

The NoSQL DMS 105 might access NoSQL database(s) 110 that is managed by the NoSQL DMS 105, and might perform a search of the NoSQL database(s) 110, by searching for each of the one or more search terms in the plurality of metadata tags associated with each medical image file among the plurality of medical image files (i.e., medical image data 115, or the like) in the NoSQL database(s) 110. In some embodiments, performing the search of the NoSQL database may comprise performing metadata search associated with the plurality of medical image files across a plurality of subjects based on attributes of medical image files and without searching based on patient data one subject at a time, each medical image file being defined as a root node of each data structure and each corresponding subject associated with a medical image file being defined as a subordinate node of the data structure. Based on a determination that at least one metadata tag associated with one or more second medical image files among the plurality of medical image files contains keywords that correspond to or match at least one search term among the one or more search terms, the NoSQL DMS 105 might identify corresponding one or more second medical image files (i.e., medical image data 130, or the like) as stored in the SQL database(s) 125, where the search of the NoSQL database(s) 110 serves as an index search of the SQL database(s) 125—due to the mirrored data 115 and 130 stored in the NoSQL and SQL databases 110 and 125. At least one of the NoSQL DMS 105 and/or the SQL DMS 120 might retrieve, from the SQL database(s) 125, the one or more second medical image files, and might send the retrieved one or more second medical image files to the requesting device 160. In some instances, sending the retrieved one or more second medical image files to the requesting device may, alternatively or additionally, comprise sending, with the at least one of the NoSQL DMS 105 or the SQL DMS 120, a list of relevant search results to the requesting device, the list of relevant search results comprising the retrieved one or more second medical image files, wherein the retrieved one or more second medical image files may include, but is not limited to, two or more medical image files that are associated with a plurality of different patients.

In some embodiments, computing system 140 and/or web server(s) 150 (collectively, "computing system" or the like) might receive, from the requesting device 160, the request for the at least one first medical image file, and might query the NoSQL DMS 105 for the requested at least one first medical image file, by relaying the request to the NoSQL DMS 105. In some cases, the computing system might present the UI 175 via the requesting device 160. In such cases, the request might be received via the UI 175. In some instances, sending the retrieved one or more second medical image files to the requesting device may comprise displaying the retrieved one or more second medical image files in the UI 175.

According to some embodiments, the computing system might convert the retrieved one or more second medical image files into one or more DICOM-compliant search results. In some cases, displaying the retrieved one or more second medical image files in the UI 175 may comprise displaying the retrieved one or more second medical image files as the converted one or more DICOM-compliant search results in the UI 175. In some instances, based on a determination that a user's mouse cursor is hovering over a DICOM-compliant search result, the computing system might generate and display a pop-up display indicating specific information or values associated with the DICOM-compliant search result, based at least in part on the one or more search terms.

In some embodiments, the computing system might provide one or more task options for each of the displayed retrieved one or more second medical image files in the UI 175. In some cases, the one or more task options may include, without limitation, at least one of options to download particular one or more third medical image files among the one or more second medical image files, options to add particular one or more fourth medical image files among the one or more second medical image files to at least one project group folder, options to link together at least two fifth medical image files among the one or more second medical image files, options to export one or more sixth medical image files among the one or more second medical image files, options to share one or more seventh medical image files among the one or more second medical image files, options to upload one or more eighth medical image files, options to start a new search, options to save a current search, options to manage saved searches, options to view recent searches, options to export searches, options to open a new project folder, options to save a current project folder, options to manage project folders, options to complete a current project, options to view active projects, or options to export project folders, and/or the like.

According to some embodiments, two or more ninth medical image files among the one or more second medical image files that are obtained during a single imaging session may be grouped together as a single imaging asset with at least one of shared metadata, common metadata, or linked metadata, and/or the like. For example, in the case that a plurality of image sets is collected in a single imaging session (e.g., to understand the dynamic interactions or operations of an anatomical structure, or the like), the image discovery utility may group this plurality of image sets so as to treat them as a single image asset or a single set of image assets. In so doing, the image discovery utility may present the plurality of image sets grouped together as an asset in the UI, and may present the user with options to select each image group separately for action (such as previewing or downloading, or the like). In a non-limiting example, a cardiac computerized tomography ("CT") scan might include 10 image sets (sometimes referred to as "multiphase scans" or "multiphase images" or the like) that are collected in a single imaging session to understand a patient's heartbeat. The user may be provided with the option to supply this group of 10 image sets to the imaging discovery utility so that they may be treated as one image asset. Alternatively, or additionally, the two or more ninth medical image files may be obtained during different imaging sessions. In some embodiments, the two or more ninth medical images may be either a collection of image sets of a single anatomical structure or a collection of image sets of two or more anatomical structures (in some cases, image sets of anatomical structures throughout the body of the subject), or the like. The benefit for such functionality is that all the metadata and artifacts (or artifact files) may be linked at the image asset level. However, when viewing the asset, the UI may allow the user to see that there are multiple sets of images (whether representing a single anatomical structure or multiple anatomical structures, or the like, and/or whether obtained during a single session or multiple sessions, or the like) grouped together as the asset, and may allow the user to select each image group separately for action (e.g., for previewing or downloading, or the like).

In some cases, the one or more task options may further comprise at least one of options to preview the two or more ninth medical image files together in the UI, options to download the two or more ninth medical image files as a single set of image files, options to export the two or more ninth medical image files as a single set of image files, options to share the two or more ninth medical image files as a single set of image files, or options to edit metadata associated with each of the two or more ninth medical image files individually or as a group, and/or the like. In some instances, the one or more task options may further comprise at least one of options to perform auto-segmentation for one or more tenth medical image files among the one or more second medical image files, or options to perform auto-measurements for one or more eleventh medical image files among the one or more second medical image files, and/or the like.

In some embodiments, a model generation system (which, in some cases, might be embodied in the computing system, or the like) might generate one or more three-dimensional ("3D") models based at least in part on at least one twelfth medical image file among the retrieved one or more second medical image files.

In some aspects, based on a determination that contents of one of NoSQL database(s) 110 that is(are) managed by NoSQL DMS 105 or SQL database 125 that is managed by SQL DMS 120 have changed, the system (i.e., at least one of NoSQL DMS 105, SQL DMS 120, computing system 140, and/or web server(s) 150, or the like; also referred to herein as "image discovery utility" or the like) might autonomously mirror the changed contents in the other of the NoSQL database 110 or the SQL database 125.

Alternatively, or additionally, according to some aspects, the system (i.e., at least one of NoSQL DMS 105, SQL DMS 120, computing system 140, and/or web server(s) 150, or the like; also referred to herein as "image discovery utility" or the like) might receive a request to modify metadata attributes associated with a medical image file that is stored and mirrored in each of a NoSQL database managed by the NoSQL DMS and a SQL database managed by the SQL DMS. The system may present a UI with options for the user to dynamically modify metadata attributes associated with the medical image file, wherein the options to dynamically modify metadata attributes may include, without limitation, at least one of dynamically adding group specific metadata attributes to metadata fields of the medical image file, dynamically modifying group specific metadata attributes in metadata fields of the medical image file, dynamically deleting group specific metadata attributes in metadata fields of the medical image file, dynamically defining new group specific metadata fields of the medical image file, dynamically modifying group specific metadata fields of the medical image file, dynamically deleting group specific metadata fields of the medical image file, or dynamically linking a metadata field with one or more artifact files, and/or the like. In response to receiving user input based on the presented options to dynamically modify metadata attributes associated with the medical image file, the system may update at least one of group specific metadata fields or group specific metadata attributes associated with the medical image file in one of the NoSQL database or the SQL database, and may mirror changes to the at least one of group specific metadata fields or group specific metadata attributes associated with the medical image file in the other of the NoSQL database or the SQL database.

Alternatively, or additionally, in some aspects, the system (i.e., at least one of NoSQL DMS 105, SQL DMS 120, computing system 140, and/or web server(s) 150, or the like; also referred to herein as "image discovery utility" or the like) might receive a request to associate one or more artifact files with a metadata attribute associated with a medical image file that is stored and mirrored in each of a NoSQL database managed by the NoSQL DMS and a SQL database managed by the SQL DMS. The system might present a UI with options for the user to modify the metadata attribute associated with the medical image file to include a link between the metadata attribute with the one or more artifact files. In response to receiving user input based on the presented options to modify the metadata attribute associated with the medical image file, the system might update a metadata field associated with the metadata attribute in one of the NoSQL database or the SQL database to include the link between the metadata attribute with the one or more artifact files, and might mirror changes to at least one of the metadata field or the metadata attribute in the other of the NoSQL database or the SQL database, wherein the link between the metadata attribute with the one or more artifact files comprises a relational map between the metadata attribute and each of the one or more artifact files.

Alternatively, or additionally, according to some aspects, in response to receiving a request for at least one first medical image file, the system (i.e., at least one of NoSQL DMS 105, SQL DMS 120, computing system 140, and/or web server(s) 150, or the like; also referred to herein as "image discovery utility" or the like) might perform an index search of a NoSQL database for medical image files associated with a plurality of subjects, the NoSQL database containing a plurality of medical image files, a plurality of metadata tags associated with each medical image file, and a plurality of artifact files associated with two or more of the plurality of medical image files, the NoSQL database containing mirrored copies of the plurality of medical image files that are stored in a relational ("SQL") database that is managed by a SQL DMS. The system might retrieve the requested at least one first medical image file from the SQL database, based on the index search of the NoSQL database. In some cases, performing the index search may comprise performing metadata search associated with the plurality of medical image files across the plurality of subjects based on attributes of medical image files and without searching based on patient data one subject at a time, each medical image file being defined as a root node of each data structure and each corresponding subject associated with a medical image file being defined as a subordinate node of the data structure.

According to some aspects, the imaging discovery utility described with respect to the various embodiments addresses each of the challenges associated with conventional commercial clinical image management systems (namely, challenges in terms of labelling, mining, and associating derived artifacts or artifact files with the clinical images), by enabling dynamic tagging of imaging records, enabling searching across all images under image management (regardless of which patient the images are associated with), and enabling linking of the images to data and artifacts derived from the images. Further, some conventional commercial clinical image management systems may inherently be designed or configured to prevent cross-searching across the plurality of patients and their data as a measure to ensure compliance with privacy and security rules and protocols (such as, but not limited to, those under the Health Insurance Portability and Accountability Act of 1996 ("HIPAA"), or the like). As the imaging discovery utility, according to the various embodiments, is designed to be used primarily by healthcare professionals or medical researchers, authentication functionalities and features (such as shown and described below with respect to the authentication aspects of FIG. 2, or the like), cross-searching across the plurality of patients within the image discovery utility remains in compliance with such privacy and security rules and protocols. Even if other users utilize the imaging discovery utility, authentication processes would still avoid non-compliance with these privacy and security rules and protocols.

The solution implements the coupling of a structured and unstructured database. The structured database may contain the minimum required data fields to make the image discoverable or searchable, while the unstructured database may provide the capability to dynamically enhance or enrich data fields based on user needs or as more information is derived from the image. The data structure also links artifacts to the image, such artifacts including, but not limited to, image processing analysis files, segmentation files, three-dimensional ("3D") print files, machine learning ("ML") algorithm files, and/or the like. Searches may be performed across the data fields as well as across the associated files and artifacts. An additional feature of the system is the ability to aggregate images into sets or collections based on search criteria. The system is able to search imaging assets and related artifacts, which can be organized in a project collection. The system also allows discoverability and reuse of information and artifacts that are costly to extract from the image. The reuse of imaging provides a larger volume of evidence for research and development applications and/or for regulatory applications, while improving research and development productivity and cost avoidance arising from purchasing duplicate imaging. The system provides a rapid response to regulatory or clinical questions, while providing knowledge capture and sharing across different business units, and provides the ability to identify and strategically fill imaging needs beyond one business unit or company. Applications include creating a focused set of data with a set of common criteria on which to create or apply artificial intelligence ("AI") and/or ML methods, atlas-based segmentation methods, or other types of analytics, or the like.

These and other functions of the system 100 (and its components) are described in greater detail below with respect to FIGS. 2-5.

Figure 2:
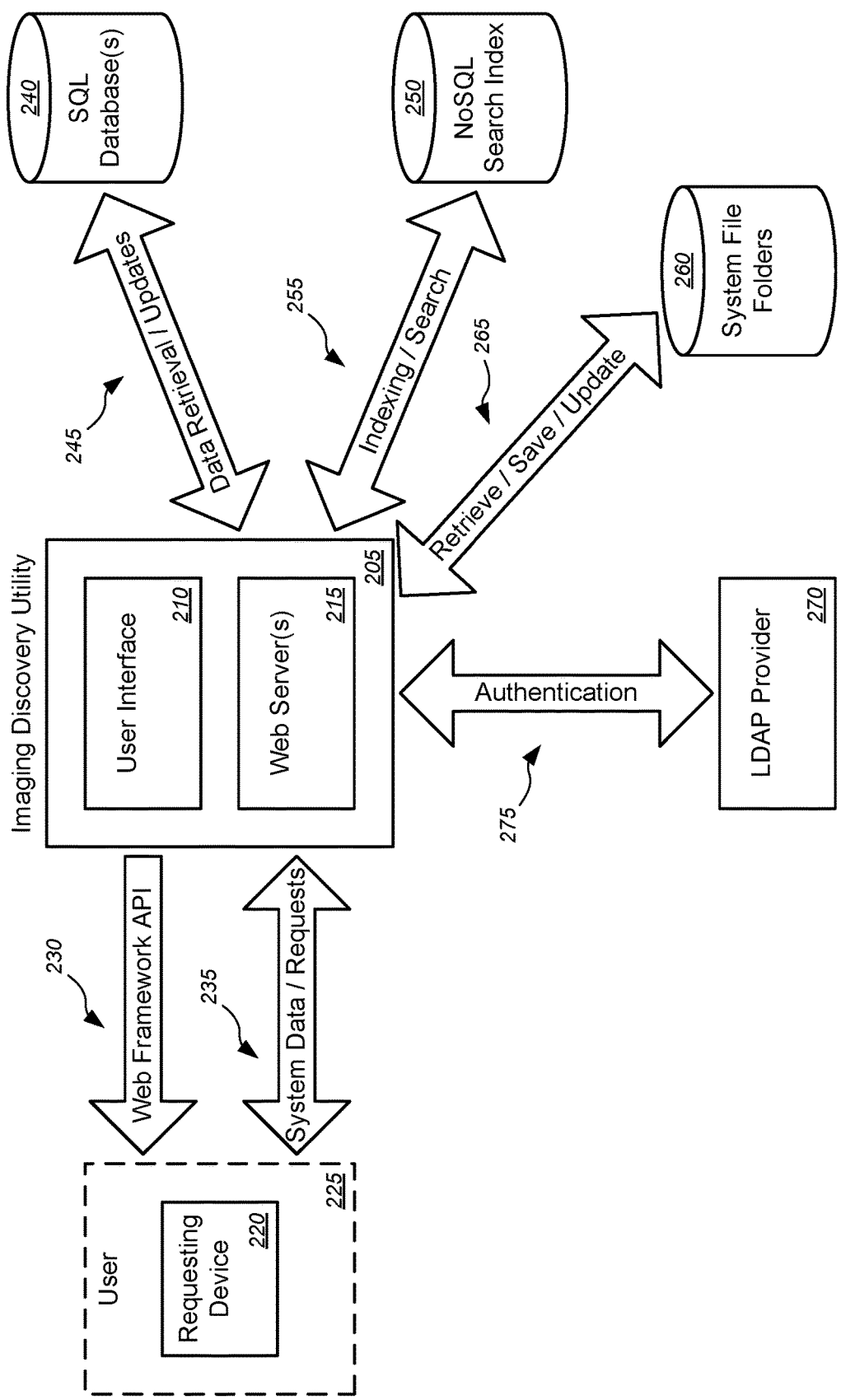
FIG. 2 is a schematic diagram illustrating a non-limiting example of interactions amongst components of a system for implementing an imaging discovery utility for augmenting clinical image management, in accordance with various embodiments.

FIG. 2 is a schematic diagram illustrating a non-limiting example of interactions amongst components of a system 200 for implementing an imaging discovery utility for augmenting clinical image management, in accordance with various embodiments.

In the non-limiting embodiment of FIG. 2, system 200 may comprise an imaging discovery utility 205, which might comprise a user interface ("UI") system 210 and/or a web server(s) 215. System 200 may further comprise a requesting device 220 associated with a user 225.

In operation, the UI system 210 and/or the imaging discovery utility 205 might establish a web framework API 230, in some cases, using a web framework (such as AngularJS or other web framework systems, or the like) to generate and present a UI to the user 225, the web framework API 230 utilizing javascript ("JS"), hypertext markup language ("HTML"), and/or cascading style sheet ("CSS"), and/or the like.

The requesting device 220 might communicate (via at least one first communications link (denoted in FIG. 2 by double-headed arrow 235), or the like) with the web server(s) 215, by sending requests (e.g., a request for at least one first medical image file, or the like) to the web server(s) 215 and receiving system data (including, but not limited to, one or more medical image files, at least one metadata tag associated with each of the one or more medical image files, or at least one artifact file associated with each of the one or more medical image files, and/or the like), or the like.

The imaging discovery utility 205 might communicate (via at least one second communications link (denoted in FIG. 2 by double-headed arrow 245), or the like) with relational ("SQL") database(s) 240, by sending updates (for updating and/or maintaining functionalities of the SQL database(s) 240, or the like) to the SQL database(s) 240 and receiving data (including, but not limited to, one or more medical image files, at least one metadata tag associated with each of the one or more medical image files, or at least one artifact file associated with each of the one or more medical image files, and/or the like) stored in the SQL database(s) 240.

The imaging discovery utility 205 might communicate (via at least one third communications link (denoted in FIG. 2 by double-headed arrow 255), or the like) with non-relational ("NoSQL") database(s) 250, by sending a search request to the SQL database(s) 250 and receiving indexing data (including, but not limited to, indexing data for one or more medical image files, indexing data for at least one metadata tag associated with each of the one or more medical image files, or indexing data for at least one artifact file associated with each of the one or more medical image files, and/or the like) from the NoSQL database(s) 250. The NoSQL database(s) 250, which may be managed by a NoSQL data management system ("DMS") (similar to NoSQL DMS 105 of FIG. 1, or the like) may contain mirrored copies of the plurality of medical image files that are stored in the SQL database(s) 240 that is managed by a SQL DMS (similar to SQL DMS 120 of FIG. 1, or the like).

The imaging discovery utility 205 might communicate (via at least one fourth communications link (denoted in FIG. 2 by double-headed arrow 265), or the like) with system file folder(s) 260, by saving and/or updating system data files to the system file folder(s) 260 and retrieving system data files from the system file folder(s) 260.

The imaging discovery utility 205 might communicate (via at least one fifth communications link (denoted in FIG. 2 by double-headed arrow 275), or the like) with lightweight directory access protocol ("LDAP") provider system 270, by exchanging authentication data with the LDAP provider system 270.

In response to receiving a request for at least one first medical image file from the requesting device 220 via the at least one first communications link, imaging discovery utility 205 might authenticate at least one of the requesting device 220, the user 225, and/or the request with the LDAP provider system 270 via the at least one fifth communications link. After authentication of the at least one of the requesting device 220, the user 225, and/or the request, the imaging discovery utility 205 might send a search request for the at least one first medical image file to the NoSQL database(s) 250 and might receive indexing data associated with the requested at least one first medical image file. As the NoSQL database(s) 250 contains mirrored copies of the plurality of medical image files that are stored in the SQL database(s) 240, the indexing data also provides information about indexing of data contained in the SQL database(s) 240. Importantly, as the NoSQL database(s) 250 provides more robust searching functionalities compared with the SQL database(s) 240, indexing of the at least one first medical image file stored in the NoSQL database(s) 250 results in effective indexing of the mirrored at least one first medical image file stored in the SQL database(s) 240. The imaging discovery utility 205 might subsequently retrieve the mirrored at least one first medical image file from the SQL database(s) 240 based on the indexing data. In response to retrieving the mirrored at least one first medical image file, the imaging discovery utility 205 might send or relay the requested at least one first medical image file to the requesting device 220 via the at least one first communications link 235.

System 200 might otherwise operate in a similar, if not identical, manner as system 100 of FIG. 1.

FIGS. 3A-3D (collectively, "FIG. 3") are schematic diagrams illustrating various non-limiting examples 300, 300', 300", and 300'" of image data library metadata that may be used when implementing an imaging discovery utility for augmenting clinical image management, in accordance with various embodiments.

With reference to FIG. 3, the various image data library metadata might be embodied as spreadsheet data containing metadata tags for one or more medical image files, although the image data library metadata is not limited to such and can be embodied as any suitable data structure or in any suitable format or file. In some embodiments, the image data library metadata may include, without limitation, one or more instructions for entering metadata or metadata tags, one or more source library metadata, one or more subject library metadata, one or more scan library metadata, and/or one or more device library metadata, or the like. According to some embodiments, the image data library metadata might include, but is not limited to, required data points (denoted in FIG. 3 by dark gray highlighting of metadata label and white colored text, or the like), group specific optional data points (denoted in FIG. 3 by light gray highlighting of metadata label and black colored text, or the like), data mined from a DICOM header of the medical image file (denoted in FIG. 3 by mid-gray highlighting of metadata label and white colored text, or the like), and/or the like. Although particular colored highlighting and particular colored text are used in FIG. 3, the various embodiments are not so limited, and any suitable highlighting or color or the like may be used to highlight or distinguish among required data points, group specific optional data points, and/or data mined from the DICOM header of the medical image file, and/or the like. Alternatively, or additionally, a data field may be used to identify metadata as being required metadata points, group specific optional metadata points, or metadata points mined from a DICOM header of the medical image file, or the like.

In some embodiments, the one or more instructions may include, without limitation, a first step of preparing assets (in this case, medical images or medical image files) within the required file structure (with a note to point to or reference a supporting document(s)), a second step of adding the assets to the data library with a supporting description(s), a third step of completing all required and flexible metadata points within the spreadsheet, and a fourth step of including any supporting file structures, and/or the like.

FIG. 3A depicts a non-limiting embodiment 300 of an example of common image data library metadata. According to some embodiments, the common image data library metadata (although not fully shown in FIG. 3A) may include, without limitation, one or more source library metadata fields, one or more subject library metadata fields, one or more scan library metadata fields, and/or one or more device library metadata (shown, e.g., in FIG. 3D), or the like.

In some instances, the one or more source library metadata fields may include, but are not limited to, a source institution metadata field (which is a text data type and is configured to contain information pertaining to a source from which the asset is received), a study code metadata field (which is a text data type and is configured to contain information pertaining to a reason for which the asset was collected), a study description metadata field (which is a text data type and is configured to contain information pertaining to a description of a reason for which the asset was collected), a source institution city metadata field (which is a text data type and is configured to contain information pertaining to a city where the source institution is geographically located), and a source geography metadata field (which is a text data type and is configured to contain information pertaining to a geographic location of the source institution), and/or the like.

In some cases, the one or more subject library metadata fields may include, without limitation, a study code metadata field (which is a text data type and is configured to contain information pertaining to a reason for which the asset was collected), a subject identification ("ID") metadata field (which is a text data type and is configured to contain information pertaining to an identifier for a scan subject), a species metadata field (which is a text data type and is configured to contain information pertaining to species of the scan subject), a gender metadata field (which is a text option data type and is configured to contain information pertaining to gender of the scan subject), a year of birth ("YOB") metadata field (which is a number data type and is configured to contain information pertaining to a year of birth of the scan subject (in some cases, expressed as a 4 digit number)), and a race metadata field (which is a text data type and is configured to contain information pertaining to race of the scan subject), and/or the like.

In some instances, the one or more scan library metadata fields may include, but are not limited to, a subject ID metadata field (which is a text data type and is configured to contain information pertaining to an identifier for a scan subject), a scan ID metadata field (which is a text data type and is configured to contain information pertaining to an identifier for the scan asset), a scan date metadata field (which is a date data type and is configured to contain information pertaining to a date the scan was collected (in some cases, expressed in terms of "mm/dd/yyyy" or any suitable date format, or the like)), a primary anatomical structure metadata field (which is a text data type and is configured to contain information pertaining to primary anatomy depicted in the scan), and an expected number of phases metadata field (which is a number data type and is configured to contain information pertaining to a number of phases that are expected or known to be reflected in the scan), and/or the like.

As shown in the FIG. 3A, the source institution metadata field, the study code metadata field, the study description metadata field, the subject ID metadata field, the species metadata field, the gender metadata field, the YOB metadata field, the race metadata field, the scan ID metadata field, the scan date metadata field, the primary anatomical structure metadata field, and the expected number of phases metadata field are marked or denoted as being required data point fields, while the source institution city metadata field and the source geography metadata field are marked or denoted as being group specific optional data point fields. Although particular metadata fields are shown in the data library as shown in FIG. 3A in particular sections (i.e., source library metadata section, subject library metadata section, scan library metadata section, etc.), the various embodiments are not so limited, and any suitable metadata fields may be used or included, and may be grouped (and in some cases, duplicated) in any suitable sections (not limited to those shown or described above with respect to FIG. 3A). Also, although particular metadata fields are marked or denoted as being one of required data point fields or group specific optional data point fields, the various embodiments are not so limited, and each metadata field may be suitably marked or denoted as any type of data point field or the like (not limited to required data point fields, group specific optional data point fields, data mined from DICOM header data point fields, and/or the like).

FIG. 3B depicts a non-limiting embodiment 300' of an example of image data library metadata for medical images or medical image files associated with cardiac rhythm and heart failure ("CRHF") therapies and procedures. According to some embodiments, the image data library metadata for medical images or medical image files associated with CRHF therapies and procedures (although not fully shown in FIG. 3B) may include, without limitation, one or more source library metadata fields (shown, e.g., in FIG. 3A), one or more subject library metadata fields (shown, e.g., in FIG. 3A), one or more scan library metadata fields, and/or one or more device library metadata (shown, e.g., in FIG. 3D), or the like.

In some instances, the one or more scan library metadata fields may include, but are not limited to, a subject ID metadata field (which is a text data type and is configured to contain information pertaining to an identifier for a scan subject), a scan ID metadata field (which is a text data type and is configured to contain information pertaining to an identifier for the scan asset), a scan date metadata field (which is a date data type and is configured to contain information pertaining to a date the scan was collected (in some cases, expressed in terms of "mm/dd/yyyy" or any suitable date format, or the like)), a primary anatomical structure metadata field (which is a text data type and is configured to contain information pertaining to primary anatomy depicted in the scan), and an expected number of phases metadata field (which is a number data type and is configured to contain information pertaining to a number of phases that are expected or known to be reflected in the scan), and/or the like. Like in the example of FIG. 3A, the subject ID metadata field, the scan ID metadata field, the scan date metadata field, the primary anatomical structure metadata field, and the expected number of phases metadata field are marked or denoted as being required data point fields.

In some cases, the one or more scan library metadata fields may further include, without limitation, a subject weight metadata field(s) (which is a measurement data type and is configured to contain information pertaining to weight of the scan subject in pounds and/or kilograms at the time of scan (in some cases, with a note indicating that the user need only provide the weight measurement in pounds or kilograms, but not both)), a subject height metadata field(s) (which is a measurement data type and is configured to contain information pertaining to height of the scan subject in inches and/or centimeters at the time of scan (in some cases, with a note indicating that the user need only provide the height measurement in inches or centimeters, but not both)), a subject body mass index ("BMI") metadata field (which is a measurement data type and is configured to contain information pertaining to the BMI of the scan subject at the time of scan), a subject scan age metadata field (which is a number data type and is configured to contain information pertaining to the age of the subject at the time of scan), a contrast metadata field (which is a text option data type and is configured to contain information pertaining to presence of contrast in the scan (in some cases, with option for yes ("Y") or no ("N"))), a quality metadata field (which is a text option data type and is configured to contain information pertaining to quality classification of the scan (in some cases, with option for high ("H"), medium ("M"), or low ("L"))), a subject healthy metadata field (which is a text option data type and is configured to contain information pertaining to subject consideration of whether the patient or scan subject is healthy at the time of scan (in some cases, with option for yes ("Y") or no ("N"))), a subject New York Heart Association ("NYHA") classification metadata field (which is a text option data type and is configured to contain information pertaining to NYHA classification of the scan subject at the time of scan), and a secondary anatomical structure(s) metadata field (which is a text list data type and is configured to contain information pertaining to a list (in some cases, a comma separated list, or the like) of secondary anatomies depicted in the scan (in some cases, with a note that the user can add multiple values within the single cell or field)), and/or the like. These metadata fields may be marked or denoted as being group specific optional data point fields (in this case, optional data point fields associated with a CRHF group).

In some instances, the one or more scan library metadata fields may include, but are not limited to, a cardiac cycle phase metadata field (which is a text data type and is configured to contain information pertaining to cardiac cycle phases (in some cases, with a note listing examples including, e.g., 10, 20, 30, multiphase, or the like)), a gated/ungated metadata field (which is a text option data type and is configured to contain information pertaining to whether a cardiac gated scan collection or a cardiac ungated scan collection was used (in some cases, with option for gated ("G") or ungated ("U"))), a comments metadata field (which is a text data type and is configured to contain information pertaining to open field comments from users or researchers), an operative interval metadata field (which is a text data type and is configured to contain information pertaining to post-operative follow-up timepoint), an indication metadata field (which is a text data type and is configured to contain information pertaining to a reason that the scan was collected), a left ventricular ejection fraction ("LVEF") metadata field (which is a measurement data type and is configured to contain information pertaining to a LVEF value (in percent) (in some cases, with a note indicating that the field must be filled with a distinct value and that ranges must be calculated to an average value, or the like), a LVEF collection modality metadata field (which is a text option data type and is configured to contain information pertaining to what type of LVEF collection modality was used (in some cases, with option for echo ("E"), ultrasound ("U"), etc.)), a left ventricular (external) end-diastolic diameter ("LVEDD") metadata field (which is a measurement data type and is configured to contain information pertaining to the LVEDD value (in millimeters)), a chest circumference metadata field(s) (which is a measurement data type and is configured to contain information pertaining to the circumference around the chest of the scan subject in inches and/or centimeters at the time of scan (in some cases, with a note indicating that the user need only provide the circumference measurement in inches or centimeters, but not both)), and an in plane pixel resolution metadata field (which is a measurement data type and is configured to contain information pertaining to in plane pixel resolution (in millimeters) (in some cases, with a note that this data will be mined from the DICOM header, unless overwritten in this field or spreadsheet as an optional data point)), and/or the like. Except for the last metadata field (which may be marked or denoted as being data mined from DICOM header data point fields), these metadata fields may be marked or denoted as being group specific optional data point fields (in this case, optional data point fields associated with a CRHF group).

Although particular metadata fields are shown in the data library as shown in FIG. 3B in particular sections (i.e., scan library metadata section, etc.), the various embodiments are not so limited, and any suitable metadata fields may be used or included, and may be grouped (and in some cases, duplicated) in any suitable sections (not limited to those shown or described above with respect to FIG. 3B). Also, although particular metadata fields are marked or denoted as being one of required data point fields, group specific optional data point fields, or data mined from DICOM header data point fields, the various embodiments are not so limited, and each metadata field may be suitably marked or denoted as any type of data point field or the like (not limited to required data point fields, group specific optional data point fields, data mined from DICOM header data point fields, and/or the like).

FIG. 3C depicts a non-limiting embodiment 300" of an example of image data library metadata for medical images or medical image files associated with structural heart-related therapies and procedures. According to some embodiments, the image data library metadata for medical images or medical image files associated with structural heart-related therapies and procedures (although not fully shown in FIG. 3C) may include, without limitation, one or more source library metadata fields (shown, e.g., in FIG. 3A), one or more subject library metadata fields (shown, e.g., in FIG. 3A), one or more scan library metadata fields, and/or one or more device library metadata (shown, e.g., in FIG. 3D), or the like.

In some instances, the one or more scan library metadata fields may include, but are not limited to, a subject ID metadata field (which is a text data type and is configured to contain information pertaining to an identifier for a scan subject), a scan ID metadata field (which is a text data type and is configured to contain information pertaining to an identifier for the scan asset), a scan date metadata field (which is a date data type and is configured to contain information pertaining to a date the scan was collected (in some cases, expressed in terms of "mm/dd/yyyy" or any suitable date format, or the like)), a primary anatomical structure metadata field (which is a text data type and is configured to contain information pertaining to primary anatomy depicted in the scan), and an expected number of phases metadata field (which is a number data type and is configured to contain information pertaining to a number of phases that are expected or known to be reflected in the scan), and/or the like. Like in the example of FIG. 3A or FIG. 3B, the subject ID metadata field, the scan ID metadata field, the scan date metadata field, the primary anatomical structure metadata field, and the expected number of phases metadata field are marked or denoted as being required data point fields.

In some cases, the one or more scan library metadata fields may further include, without limitation, a subject weight metadata field(s) (which is a measurement data type and is configured to contain information pertaining to weight of the scan subject in pounds and/or kilograms at the time of scan (in some cases, with a note indicating that the user need only provide the weight measurement in pounds or kilograms, but not both)), a subject height metadata field(s) (which is a measurement data type and is configured to contain information pertaining to height of the scan subject in inches and/or centimeters at the time of scan (in some cases, with a note indicating that the user need only provide the height measurement in inches or centimeters, but not both)), a subject body mass index ("BMI") metadata field (which is a measurement data type and is configured to contain information pertaining to the BMI of the scan subject at the time of scan), a subject scan age metadata field (which is a number data type and is configured to contain information pertaining to the age of the subject at the time of scan), a contrast metadata field (which is a text option data type and is configured to contain information pertaining to presence of contrast in the scan (in some cases, with option for yes ("Y") or no ("N"))), a quality metadata field (which is a text option data type and is configured to contain information pertaining to quality classification of the scan (in some cases, with option for high ("H"), medium ("M"), or low ("L"))), a subject New York Heart Association ("NYHA") classification metadata field (which is a text option data type and is configured to contain information pertaining to NYHA classification of the scan subject at the time of scan), and a secondary anatomical structure(s) metadata field (which is a text list data type and is configured to contain information pertaining to a list (in some cases, a comma separated list, or the like) of secondary anatomies depicted in the scan (in some cases, with a note that the user can add multiple values within the single cell or field), and/or the like. These metadata fields may be marked or denoted as being group specific optional data point fields (in this case, optional data point fields associated with a structural heart group).

In some instances, the one or more scan library metadata fields may include, but are not limited to, a cardiac cycle phase metadata field (which is a text data type and is configured to contain information pertaining to cardiac cycle phases (in some cases, with a note listing examples including, e.g., 10, 20, 30, multiphase, or the like)), a gated/ungated metadata field (which is a text option data type and is configured to contain information pertaining to whether a cardiac gated scan collection or a cardiac ungated scan collection was used (in some cases, with option for gated ("G") or ungated ("U"))), a comments metadata field (which is a text data type and is configured to contain information pertaining to open field comments from users or researchers), an operative interval metadata field (which is a text data type and is configured to contain information pertaining to post-operative follow-up timepoint), an indication metadata field (which is a text data type and is configured to contain information pertaining to a reason that the scan was collected), a left ventricular ejection fraction ("LVEF") metadata field (which is a measurement data type and is configured to contain information pertaining to a LVEF value (in percent) (in some cases, with a note indicating that the field must be filled with a distinct value and that ranges must be calculated to an average value, or the like), a LVEF collection modality metadata field (which is a text option data type and is configured to contain information pertaining to what type of LVEF collection modality was used (in some cases, with option for echo ("E"), ultrasound ("U"), etc.)), and a left ventricular (external) end-diastolic diameter ("LVEDD") metadata field (which is a measurement data type and is configured to contain information pertaining to the LVEDD value (in millimeters)), and/or the like. These metadata fields may be marked or denoted as being group specific optional data point fields (in this case, optional data point fields associated with a structural heart group).

In some cases, the one or more scan library metadata fields may further include, without limitation, an aortic valve peak gradient metadata field(s) (which is a measurement data type and is configured to contain information pertaining to the peak pressure gradient (in mmHg) across the aortic valve), an aortic valve mean gradient metadata field(s) (which is a measurement data type and is configured to contain information pertaining to the mean pressure gradient (in mmHg) across the aortic valve), an aortic valve peak velocity metadata field(s) (which is a measurement data type and is configured to contain information pertaining to the aortic valve peak or jet velocity (in m/s)), an aortic valve area metadata field(s) (which is a measurement data type and is configured to contain information pertaining to the aortic valve area (in cm$^2$)), an aortic regurgitation metadata field (which is a text data type and is configured to contain information pertaining to amount of aortic regurgitation), a mitral valve peak gradient metadata field(s) (which is a measurement data type and is configured to contain information pertaining to the peak pressure gradient (in mmHg) across the mitral valve), a mitral valve mean gradient metadata field(s) (which is a measurement data type and is configured to contain information pertaining to the mean pressure gradient (in mmHg) across the mitral valve), a mitral valve peak velocity metadata field(s) (which is a measurement data type and is configured to contain information pertaining to the mitral valve peak or jet velocity (in m/s)), a mitral valve area metadata field(s) (which is a measurement data type and is configured to contain information pertaining to the mitral valve area (in cm$^2$)), a mitral regurgitation metadata field (which is a text data type and is configured to contain information pertaining to amount of mitral regurgitation), a pulmonary valve peak gradient metadata field(s) (which is a measurement data type and is configured to contain information pertaining to the peak pressure gradient (in mmHg) across the pulmonary valve), a pulmonary valve mean gradient metadata field(s) (which is a measurement data type and is configured to contain information pertaining to the mean pressure gradient (in mmHg) across the pulmonary valve), a pulmonary valve peak velocity metadata field(s) (which is a measurement data type and is configured to contain information pertaining to the pulmonary valve peak or jet velocity (in m/s)), a pulmonary valve area metadata field(s) (which is a measurement data type and is configured to contain information pertaining to the pulmonary valve area (in cm$^2$)), a pulmonary regurgitation metadata field (which is a text data type and is configured to contain information pertaining to amount of pulmonary regurgitation), a tricuspid valve peak gradient metadata field(s) (which is a measurement data type and is configured to contain information pertaining to the peak pressure gradient (in mmHg) across the tricuspid valve), a tricuspid valve mean gradient metadata field(s) (which is a measurement data type and is configured to contain information pertaining to the mean pressure gradient (in mmHg) across the tricuspid valve), a tricuspid valve peak velocity metadata field(s) (which is a measurement data type and is configured to contain information pertaining to the tricuspid valve peak or jet velocity (in m/s)), a tricuspid valve area metadata field(s) (which is a measurement data type and is configured to contain information pertaining to the tricuspid valve area (in cm$^2$)), and a tricuspid regurgitation metadata field (which is a text data type and is configured to contain information pertaining to amount of tricuspid regurgitation), and/or the like. These metadata fields may be marked or denoted as being group specific optional data point fields (in this case, optional data point fields associated with a structural heart group).

Although particular metadata fields are shown in the data library as shown in FIG. 3C in particular sections (i.e., scan library metadata section, etc.), the various embodiments are not so limited, and any suitable metadata fields may be used or included, and may be grouped (and in some cases, duplicated) in any suitable sections (not limited to those shown or described above with respect to FIG. 3C). Also, although particular metadata fields are marked or denoted as being one of required data point fields or group specific optional data point fields, the various embodiments are not so limited, and each metadata field may be suitably marked or denoted as any type of data point field or the like (not limited to required data point fields, group specific optional data point fields, data mined from DICOM header data point fields, and/or the like).

FIG. 3D depicts a non-limiting embodiment 300' of an example of image data library metadata for medical images or medical image files associated with neurological therapies and procedures. According to some embodiments, the image data library metadata for medical images or medical image files associated with neurological therapies and procedures (although not fully shown in FIG. 3D) may include, without limitation, one or more source library metadata fields (shown, e.g., in FIG. 3A), one or more subject library metadata fields (shown, e.g., in FIG. 3A), one or more scan library metadata fields, and/or one or more device library metadata, or the like.

In some instances, the one or more scan library metadata fields may include, but are not limited to, a subject ID metadata field (which is a text data type and is configured to contain information pertaining to an identifier for a scan subject), a scan ID metadata field (which is a text data type and is configured to contain information pertaining to an identifier for the scan asset), a scan date metadata field (which is a date data type and is configured to contain information pertaining to a date the scan was collected (in some cases, expressed in terms of "mm/dd/yyyy" or any suitable date format, or the like)), a primary anatomical structure metadata field (which is a text data type and is configured to contain information pertaining to primary anatomy depicted in the scan), and an expected number of phases metadata field (which is a number data type and is configured to contain information pertaining to a number of phases that are expected or known to be reflected in the scan), and/or the like. Like in the example of FIG. 3A, FIG. 3B, or FIG. 3C, the subject ID metadata field, the scan ID metadata field, the scan date metadata field, the primary anatomical structure metadata field, and the expected number of phases metadata field are marked or denoted as being required data point fields.

In some cases, the one or more scan library metadata fields may further include, without limitation, a subject weight metadata field(s) (which is a measurement data type and is configured to contain information pertaining to weight of the scan subject in pounds and/or kilograms at the time of scan (in some cases, with a note indicating that the user need only provide the weight measurement in pounds or kilograms, but not both)), a subject height metadata field(s) (which is a measurement data type and is configured to contain information pertaining to height of the scan subject in inches and/or centimeters at the time of scan (in some cases, with a note indicating that the user need only provide the height measurement in inches or centimeters, but not both)), a subject body mass index ("BMI") metadata field (which is a measurement data type and is configured to contain information pertaining to the BMI of the scan subject at the time of scan), a subject scan age metadata field (which is a number data type and is configured to contain information pertaining to the age of the subject at the time of scan), a contrast metadata field (which is a text option data type and is configured to contain information pertaining to presence of contrast in the scan (in some cases, with option for yes ("Y") or no ("N"))), a quality metadata field (which is a text option data type and is configured to contain information pertaining to quality classification of the scan (in some cases, with option for high ("H"), medium ("M"), or low ("L"))), and a subject healthy metadata field (which is a text option data type and is configured to contain information pertaining to subject consideration of whether the patient or scan subject is healthy at the time of scan (in some cases, with option for yes ("Y") or no ("N"))), and/or the like. These metadata fields may be marked or denoted as being group specific optional data point fields (in this case, optional data point fields associated with a neurological group).

In some instances, the one or more scan library metadata fields may include, but are not limited to, an in plane pixel resolution metadata field (which is a measurement data type and is configured to contain information pertaining to in plane pixel resolution (in millimeters)), a slice thickness metadata field (which is a measurement data type and is configured to contain information pertaining to slice thickness (in millimeters)), an increment metadata field (which is a measurement data type and is configured to contain information pertaining to increment), a modality metadata field (which is a text option data type and is configured to contain information pertaining to modality), a resolution metadata field (which is a number data type and is configured to contain information pertaining to resolution), a number of frames per slice metadata field (which is a number data type and is configured to contain information pertaining to the number of frames per slice), a source scanner metadata field (which is a text data type and is configured to contain information pertaining to the source scanner), and a number of frames metadata field (which is a number data type and is configured to contain information pertaining to the number of frames), and/or the like. These metadata fields may be marked or denoted as being data mined from DICOM header data point fields. In some cases, each of these metadata fields may include a note that the data in the corresponding field will be mined from the DICOM header, unless overwritten in said field or spreadsheet as an optional data point, and/or the like.

In some cases, the one or more device library metadata fields may further include, without limitation, a subject ID metadata field (which is a text data type and is configured to contain information pertaining to an identifier for a scan subject), a scan ID metadata field (which is a text data type and is configured to contain information pertaining to an identifier for the scan asset), a scan date metadata field (which is a date data type and is configured to contain information pertaining to a date the scan was collected (in some cases, expressed in terms of "mm/dd/yyyy" or any suitable date format, or the like)), and/or the like. These metadata fields may be marked or denoted as being required data point fields.

Although particular metadata fields are shown in the data library as shown in FIG. 3D in particular sections (i.e., scan library metadata section, device library metadata section, etc.), the various embodiments are not so limited, and any suitable metadata fields may be used or included, and may be grouped (and in some cases, duplicated) in any suitable sections (not limited to those shown or described above with respect to FIG. 3D). Also, although particular metadata fields are marked or denoted as being one of required data point fields, group specific optional data point fields, or data mined from DICOM header data point fields the various embodiments are not so limited, and each metadata field may be suitably marked or denoted as any type of data point field or the like (not limited to required data point fields, group specific optional data point fields, data mined from DICOM header data point fields, and/or the like).

FIGS. 4A-4L (collectively, "FIG. 4") are schematic diagrams illustrating various non-limiting examples 400 of user interfaces ("UIs") 405-460 that may be used when implementing an imaging discovery utility for augmenting clinical image management, in accordance with various embodiments. The UIs shown in FIG. 4 contain example subject information that are not associated with any actual or living patient or subject, but are merely provided to give context and to illustrate concepts that are part of the UIs.

Figure 4A:
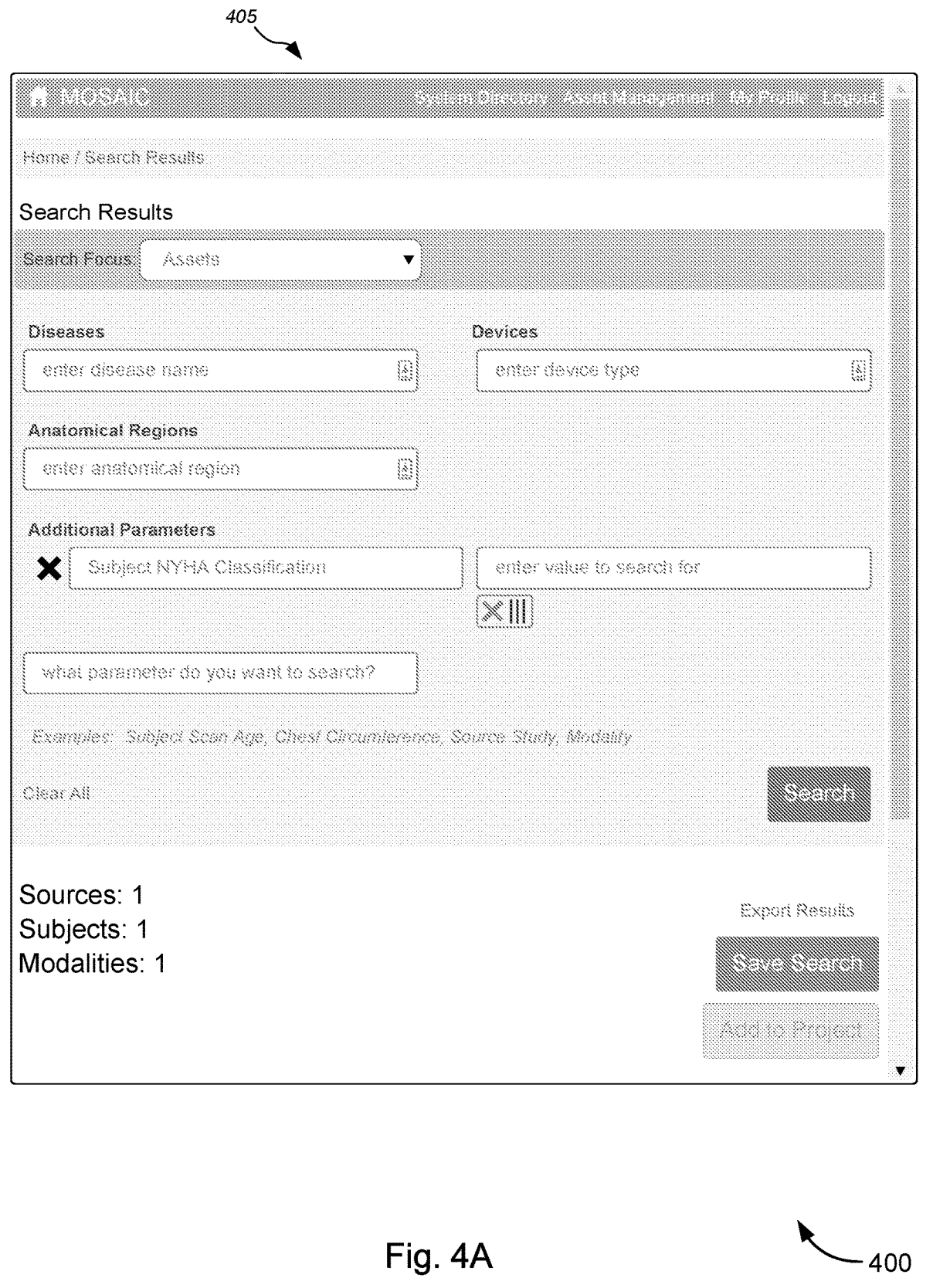

According to some embodiments, the UIs may provide the user with options to search for assets (i.e., medical images or medical image files, etc.) in the image discovery utility (which may also be referred to herein as "Medtronic Online Sharing of Anatomical Imaging Collections" or "MOSAIC" or the like), by searching by at least one of diseases, devices, anatomical regions, and/or additional parameters (including, but not limited to, source study description, project start date, secondary anatomical structure(s), source study or trial, source study ID, source study date, and/or clinical trial study center, etc.), and/or the like (such as shown in FIGS. 4A, 4B, and 4K, or the like). The UIs may further provide the user with options to initiate the search based on the input parameters, to clear all fields, to export results, to save the search, to add the search or search results to a project, to manage saved searches, and/or the like (such as shown in FIGS. 4A-4C, 4K, and 4L, or the like).

Figure 4E:
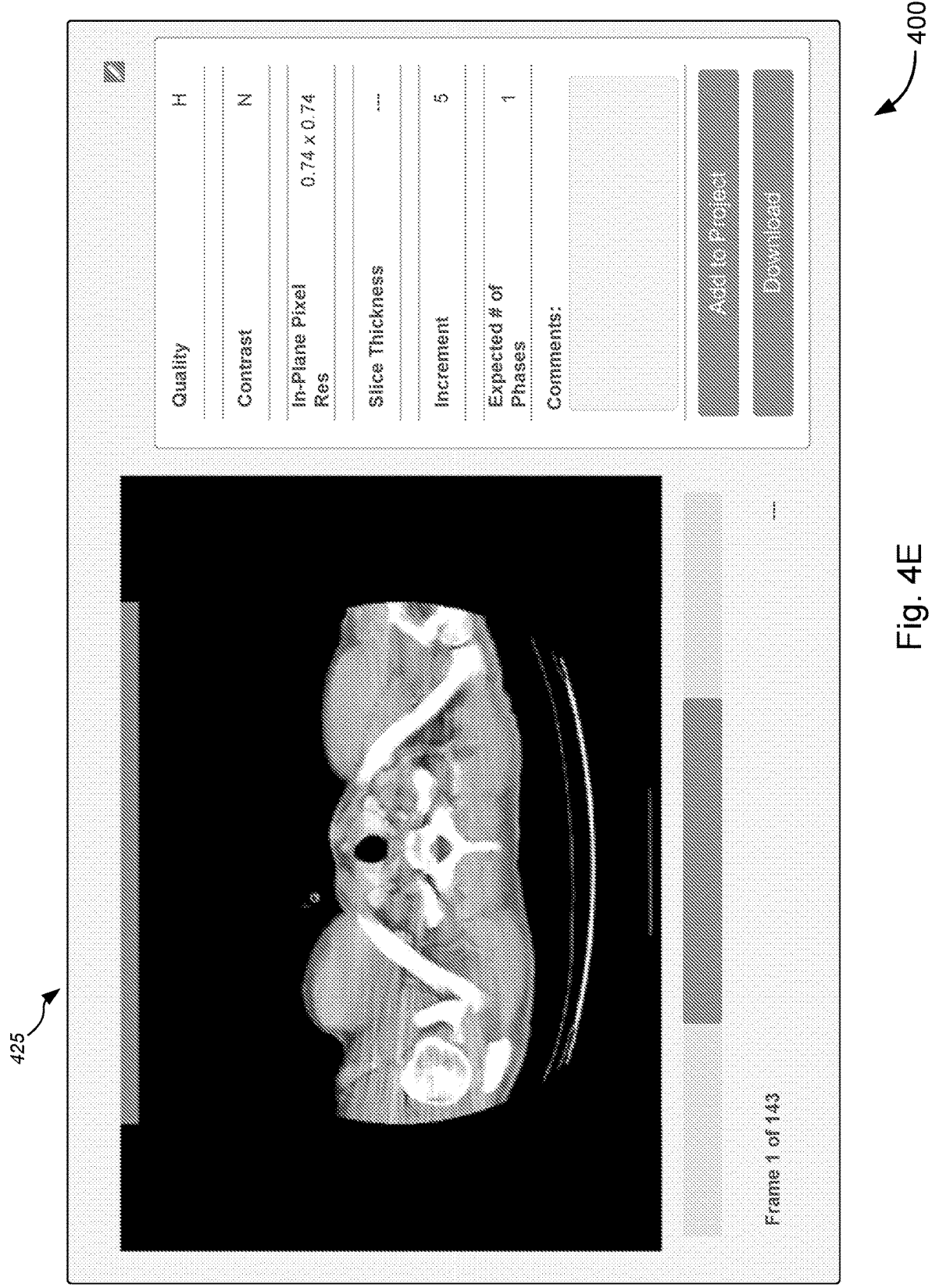
Figure 4F:
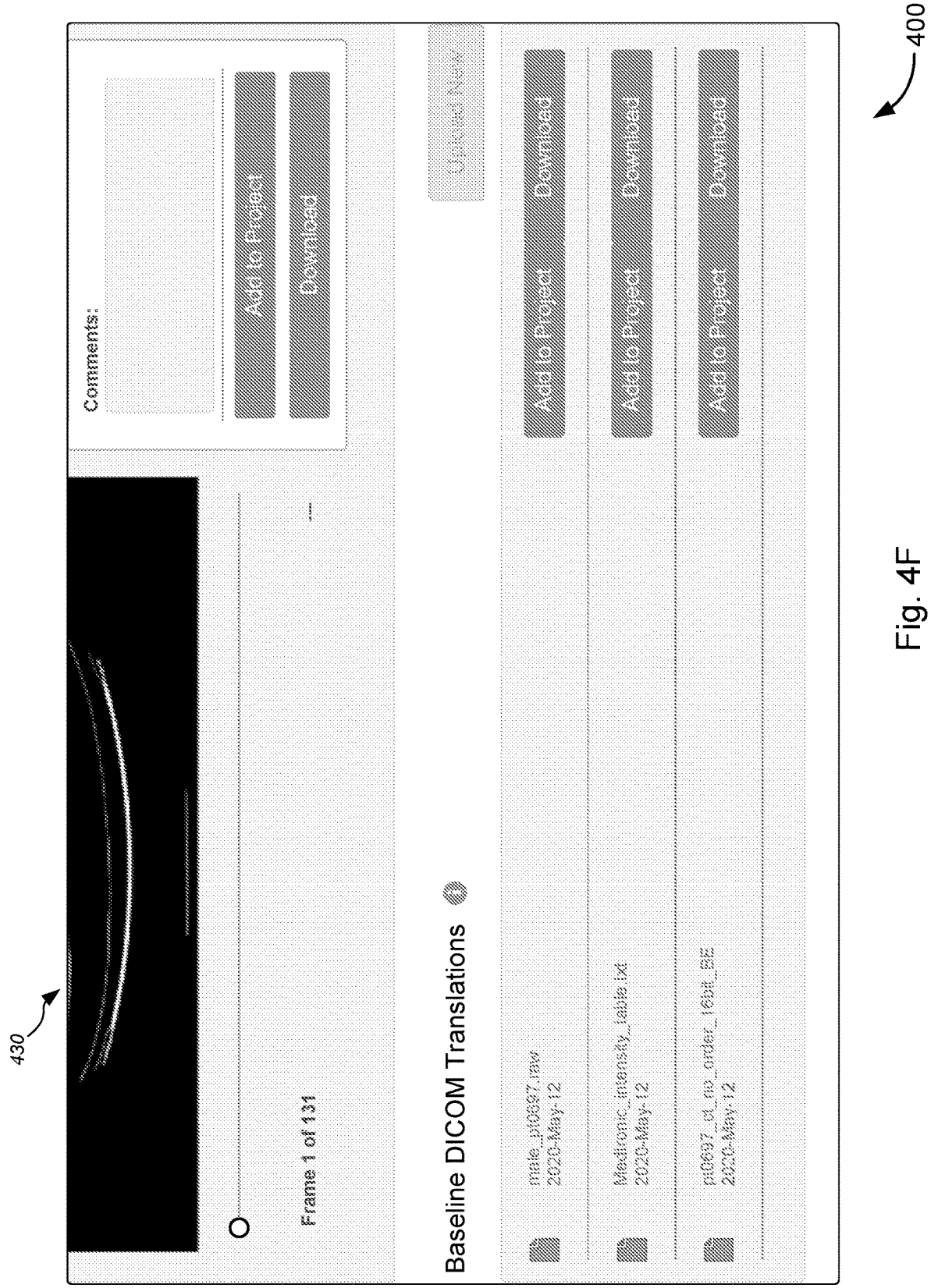
Figure 4G:
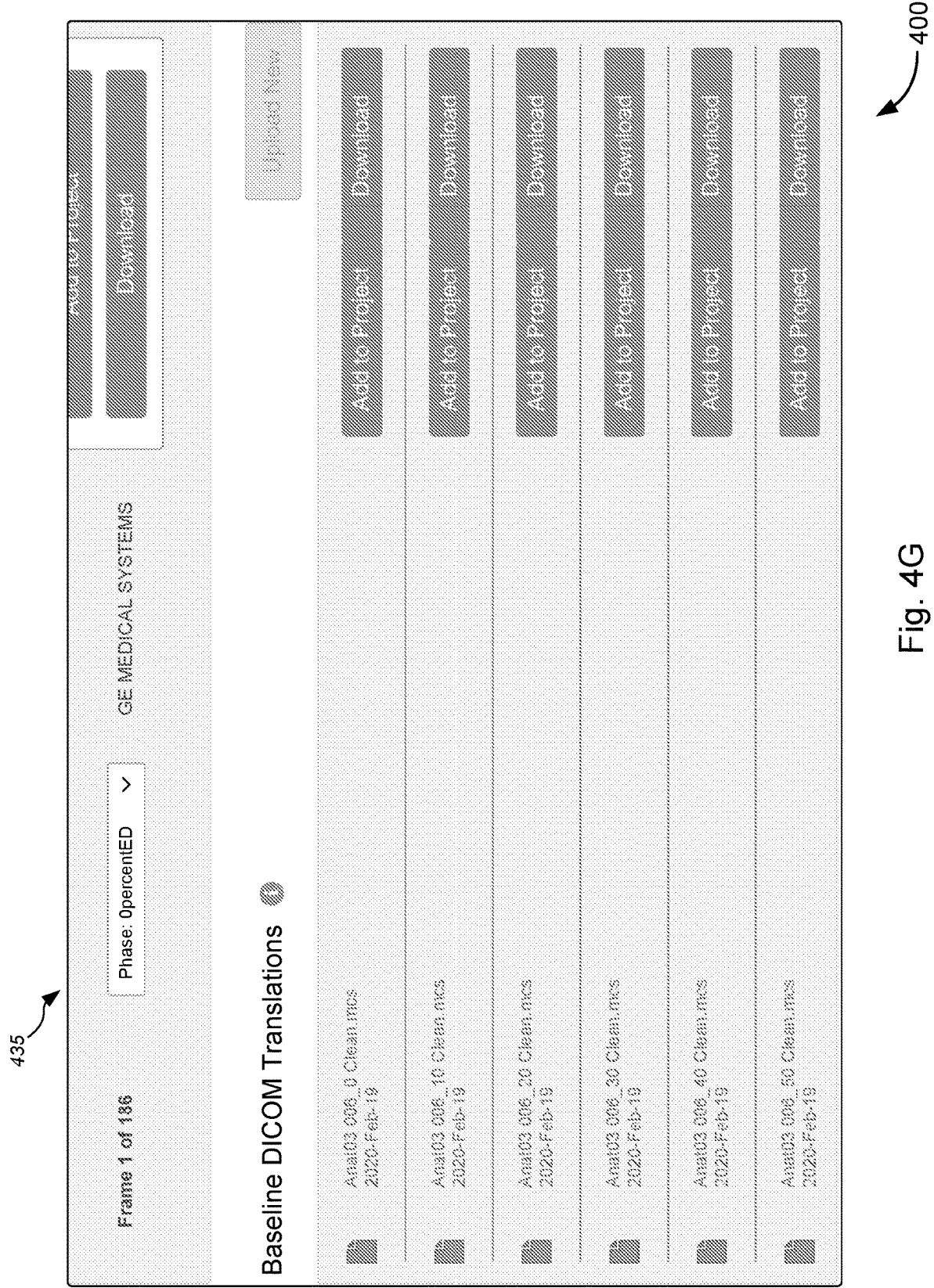
Figure 4H:
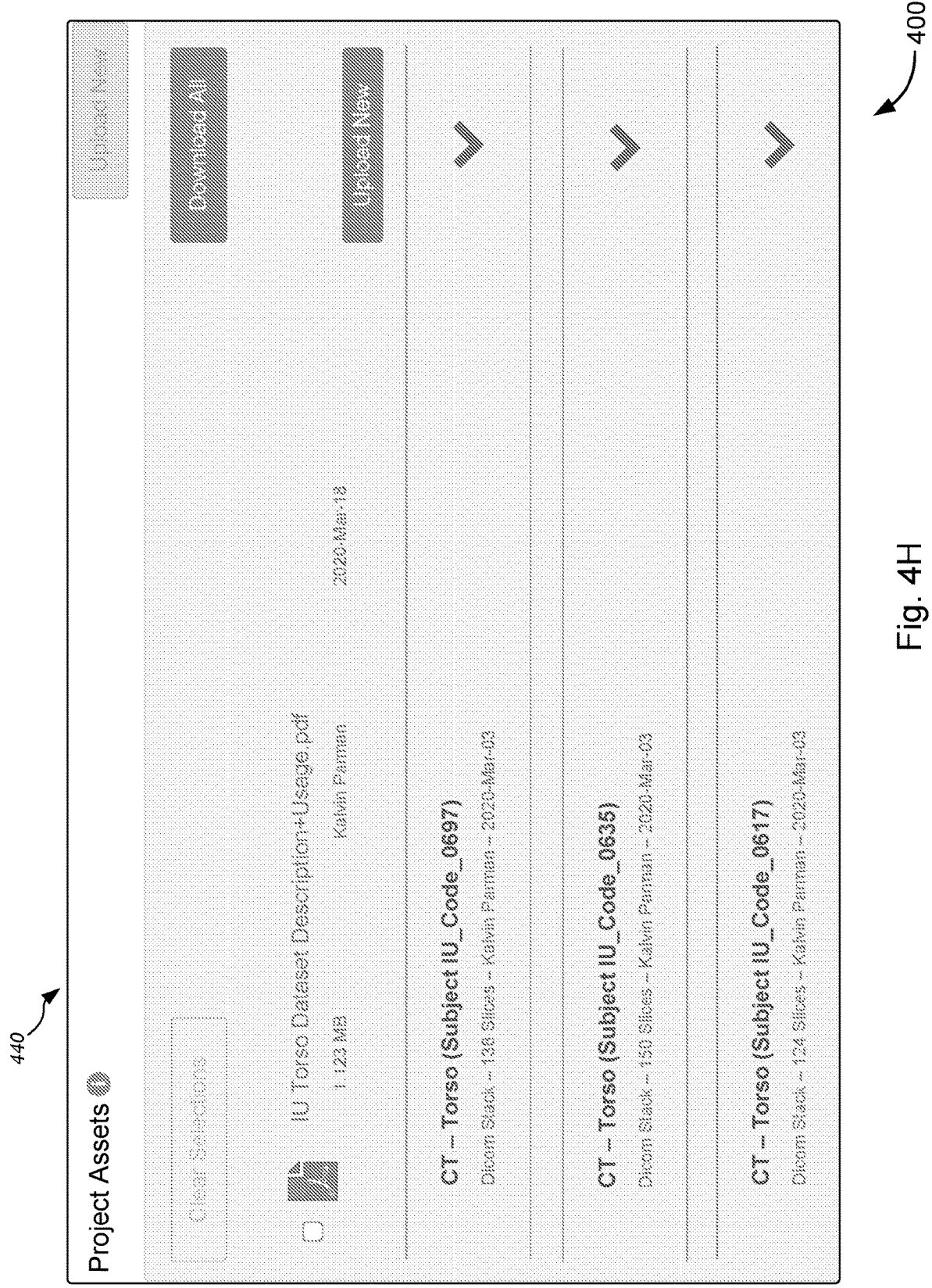
Figure 4J:
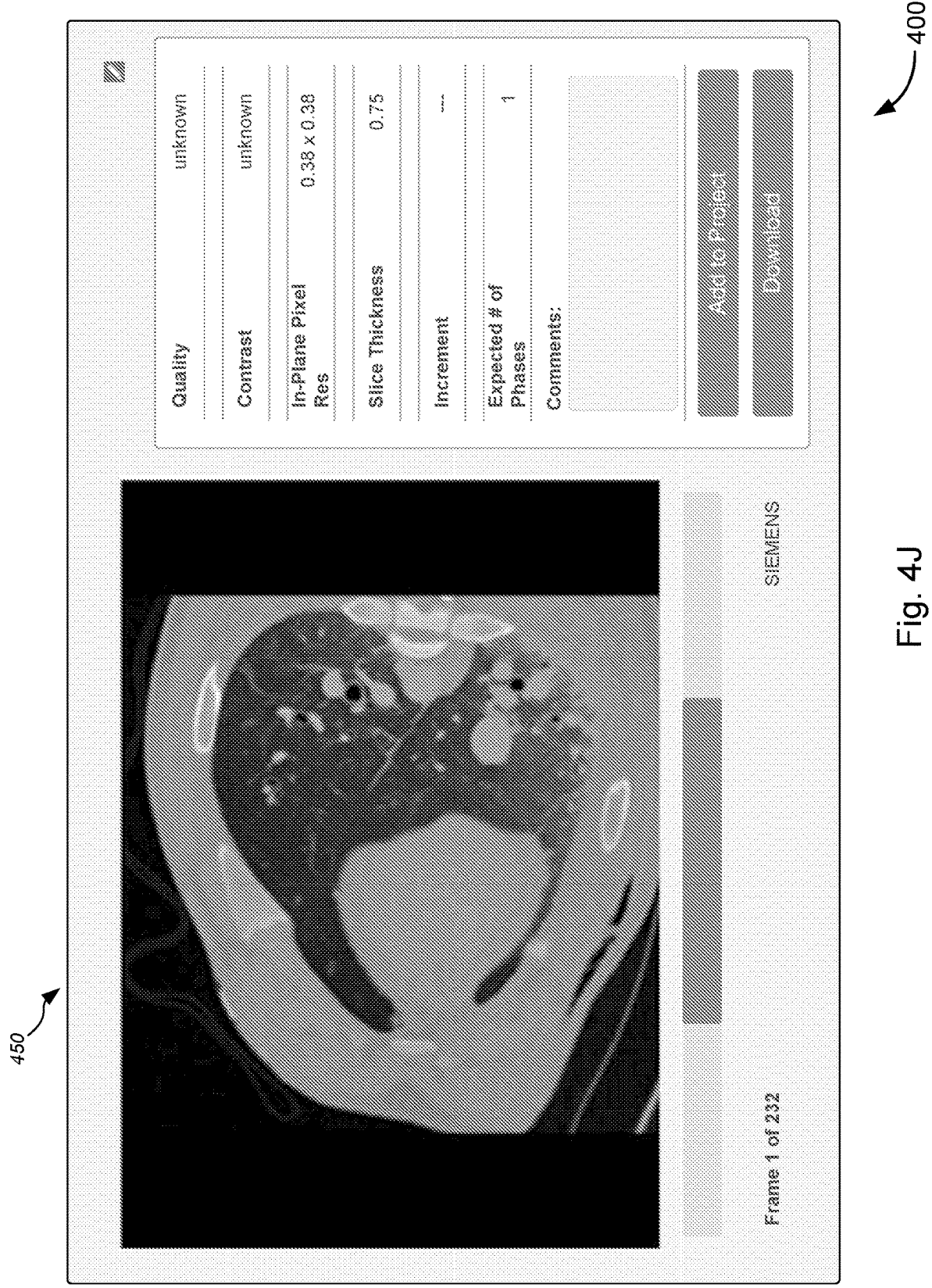
Figure 4L:

As shown in the non-limiting embodiment of FIG. 4C or FIG. 4L, because the assets (i.e., medical images or medical image files) are at the top of the hierarchy of the image-centric hierarchical system (as described above with respect to FIG. 1, or the like), the image discovery utility is able to search for related or similar images of anatomical structures (or the like) across a plurality of patients or subjects (which conventional data management systems because such conventional systems are patient-centric hierarchical systems that are inherently restricted into searching only patient information, with lower level images associated with each patient being difficult if not impossible to search, much less compile across a plurality of patients or subjects). In this manner, the image discovery utility and functionality described herein (and according to the various embodiments) enable robust and complete searching of related or similar images of anatomical structures or other image assets across a plurality of patients, thereby facilitating research and development of diagnoses, therapies, procedures, and/or pharmaceutical products, and/or the like.

As shown in the non-limiting example of UI 420 in FIG. 4D, the UI may display or otherwise present information about the asset (in this case, "Scan 1923," which is an image of a computerized tomography ("CT") scan of a torso of a subject or patient, in this case, the subject associated with anonymous alphanumeric code, "IU_Code_0697"). In some instances, the information that is presented in the UI (e.g., UI 420 of FIG. 4D, or the like) may include, without limitation, scan ID (in this case, "Scan 1923" or the like), study description (in this case, "CT—Torso" or the like), primary anatomical structure (in this case, "Torso" or the like), scan date (in this case, "2020-03-29" or the like), subject ID (in this case, "IU_Code_0697" or the like), species (in this case, "Human" or the like), gender (in this case, "Male" or the like), year of birth ("YOB"), race (in this case, "Caucasian" or the like), subject weight (in this case, "165.72 lbs" or the like), subject height (in this case, "5 foot, 11 inches" or the like), subject BMI (in this case, "23.1" or the like), subject scan age (in this case, "34 years old" or the like), subject NYHA classification (in this case, blank or not applicable), study code (in this case, "IU_CT_Torso_FY20Q1" or the like), source institution (in this case, "Center 2" or the like), division or group code (in this case, "Core Test Group" or the like), known diseases (in this case, none), and/or scanned devices (in this case, none), and/or the like.

As shown in the non-limiting example of UI 425 in FIG. 4E, the UI may display or otherwise present information about the asset. In some cases, the information that is presented in the UI (e.g., UI 425 of FIG. 4E, or the like) may include, but is not limited to, the asset(s) itself (i.e., medical image(s) or medical image file(s), or the like), quality (in this case, "High" or "H" or the like), contrast (in this case, "No" or "N" or the like), in-plane pixel resolution (in this case, "0.74×0.74" or the like), slice thickness, increment (in this case, "5" or the like), and/or expected number of phases (in this case, "1" or the like), and/or the like. In some instances, the UI may display or otherwise present at least one of a comments field for the user to input comments about the asset or subject, an option to add the asset(s) to a project(s), and/or an option to download the asset(s), and/or the like. According to some embodiments, the image discovery utility may group assets. For example, in the case that a plurality of image sets is collected in a single imaging session (e.g., to understand the dynamic interactions or operations of an anatomical structure, or the like; sometimes referred to as "multiphase scans" or "multiphase images" or the like), the image discovery utility may group this plurality of image sets so as to treat them as a single image asset or a single set of image assets. Alternatively, or additionally, the plurality of image sets may be obtained during different imaging sessions. In some embodiments, the plurality of image sets may be either a collection of image sets of a single anatomical structure or a collection of image sets of two or more anatomical structures (in some cases, image sets of anatomical structures throughout the body of the subject), or the like. In so doing, the image discovery utility may present the plurality of image sets (whether representing a single anatomical structure or multiple anatomical structures, or the like, and/or whether obtained during a single session or multiple sessions, or the like) grouped together as an asset in the UI, and may present the user with options to select each image group separately for action (such as previewing or downloading, or the like). As shown in FIG. 4E, the asset contains 143 frames or images of the anatomical structure.

As shown in the non-limiting example of UI 430 in FIG. 4F or UI 435 in FIG. 4G, the UI may display or otherwise present information, including, but not limited to, baseline DICOM translations (including, without limitation, .raw files, .txt files, .mcs files, etc.), or the like. The UI may also present at least one of options for the user to enter comments about the asset(s) or patient, options to add the asset(s) to a project(s), options to download the asset(s), options to upload new DICOM translations, options to add one or more DICOM translations to a project(s), and/or options to download one or more DICOM translations, and/or the like.

As shown in the non-limiting example of UI 440 in FIG. 4H, the UI may display or otherwise present information, including, but not limited to, Project Assets, or the like. The UI may also present at least one of options to upload new project assets, options to select project assets, options to clear selections, options to download all selected project assets, options to download all project assets, options to upload new assets within selected projects, and/or options to expand/collapse view of particular assets or project assets, and/or the like.

FIGS. 4I-4L depict non-limiting examples of UIs 445-460 that display or otherwise present information for non-human scans or medical images (in this case, medical images or medical image files of pigs, although not limited to this particular species). For example, as shown in the non-limiting example of UI 445 in FIG. 4I, the UI may display or otherwise present information about the asset (in this case, "Scan 314," which is an image of a computerized tomography ("CT") scan of a subject or patient (in this instance, a pig), in this case, the subject associated with anonymous alphanumeric code, "Pig_168470"). In some instances, the information that is presented in the UI (e.g., UI 445 of FIG. 4I, or the like) may include, without limitation, scan ID (in this case, "Scan 314" or the like), study description (in this case, "CT— Pig" or the like), primary anatomical structure (in this case, "Pig" or the like), scan date (in this case, "2019-12-31" or the like), subject ID (in this case, "Pig_168470" or the like), species (in this case, "Pig" or the like), gender (in this case, "Male" or the like), year of birth ("YOB"), race (in this case, "Yorkshire" or the like), subject weight (in this case, "154 lbs" or the like), subject height (in this case, blank or the like), subject BMI (in this case, blank or the like), subject scan age (in this case, "17 weeks old" or the like), subject NYHA classification (in this case, blank or not applicable), study code (in this case, "Pig" or the like), source institution (in this case, "Center 3" or the like), division or group code (in this case, "Core Test Group" or the like), known diseases (in this case, none), and/or scanned devices (in this case, none), and/or the like.

As shown in the non-limiting example of UI 450 in FIG. 4J, the UI may display or otherwise present information about the asset. In some cases, the information that is presented in the UI (e.g., UI 450 of FIG. 4J, or the like) may include, but is not limited to, the asset(s) itself (i.e., medical image(s) or medical image file(s), or the like), quality (in this case, "unknown" or the like), contrast (in this case, "unknown" or the like), in-plane pixel resolution (in this case, "0.38×0.38" or the like), slice thickness (in this case, "0.75" or the like), increment (in this case, blank or the like), and/or expected number of phases (in this case, "1" or the like), and/or the like. In some instances, the UI may display or otherwise present at least one of a comments field for the user to input comments about the asset or subject, an option to add the asset(s) to a project(s), and/or an option to download the asset(s), and/or the like. According to some embodiments, the image discovery utility may group assets. For example, in the case that a plurality of image sets is collected in a single imaging session (e.g., to understand the dynamic interactions or operations of an anatomical structure, or the like; sometimes referred to as "multiphase scans" or "multiphase images" or the like), the image discovery utility may group this plurality of image sets so as to treat them as a single image asset or a single set of image assets. Alternatively, or additionally, the plurality of image sets may be obtained during different imaging sessions. In some embodiments, the plurality of image sets may be either a collection of image sets of a single anatomical structure or a collection of image sets of two or more anatomical structures (in some cases, image sets of anatomical structures throughout the body of the subject), or the like. In so doing, the image discovery utility may present the plurality of image sets (whether representing a single anatomical structure or multiple anatomical structures, or the like, and/or whether obtained during a single session or multiple sessions, or the like) grouped together as an asset in the UI, and may present the user with options to select each image group separately for action (such as previewing or downloading, or the like). As shown in FIG. 4J, the asset contains 232 frames or images of the anatomical structure.

FIGS. 5A-5D (collectively, "FIG. 5") are flow diagrams illustrating a method 500 for implementing an imaging discovery utility for augmenting clinical image management, in accordance with various embodiments. Method 500 of FIG. 5A continues onto FIG. 5B following the circular marker denoted, "A," continues onto FIG. 5C following the circular marker denoted, "B," and/or continues onto FIG. 5D following the circular marker denoted, "C."

While the techniques and procedures are depicted and/or described in a certain order for purposes of illustration, it should be appreciated that certain procedures may be reordered and/or omitted within the scope of various embodiments. Moreover, while the method 500 illustrated by FIG. 5 can be implemented by or with (and, in some cases, are described below with respect to) the systems, examples, or embodiments 100, 200, 300, 300', 300", 300'", and 400 of FIGS. 1, 2, 3A, 3B, 3C, 3D, and 4A-4H, respectively (or components thereof), such methods may also be implemented using any suitable hardware (or software) implementation. Similarly, while each of the systems, examples, or embodiments 100, 200, 300, 300', 300", 300'", and 400 of FIGS. 1, 2, 3A, 3B, 3C, 3D, and 4A-4H, respectively (or components thereof), can operate according to the method 500 illustrated by FIG. 5 (e.g., by executing instructions embodied on a computer readable medium), the systems, examples, or embodiments 100, 200, 300, 300', 300", 300'", and 400 of FIGS. 1, 2, 3A, 3B, 3C, 3D, and 4A-4H can each also operate according to other modes of operation and/or perform other suitable procedures.

Figure 5A:
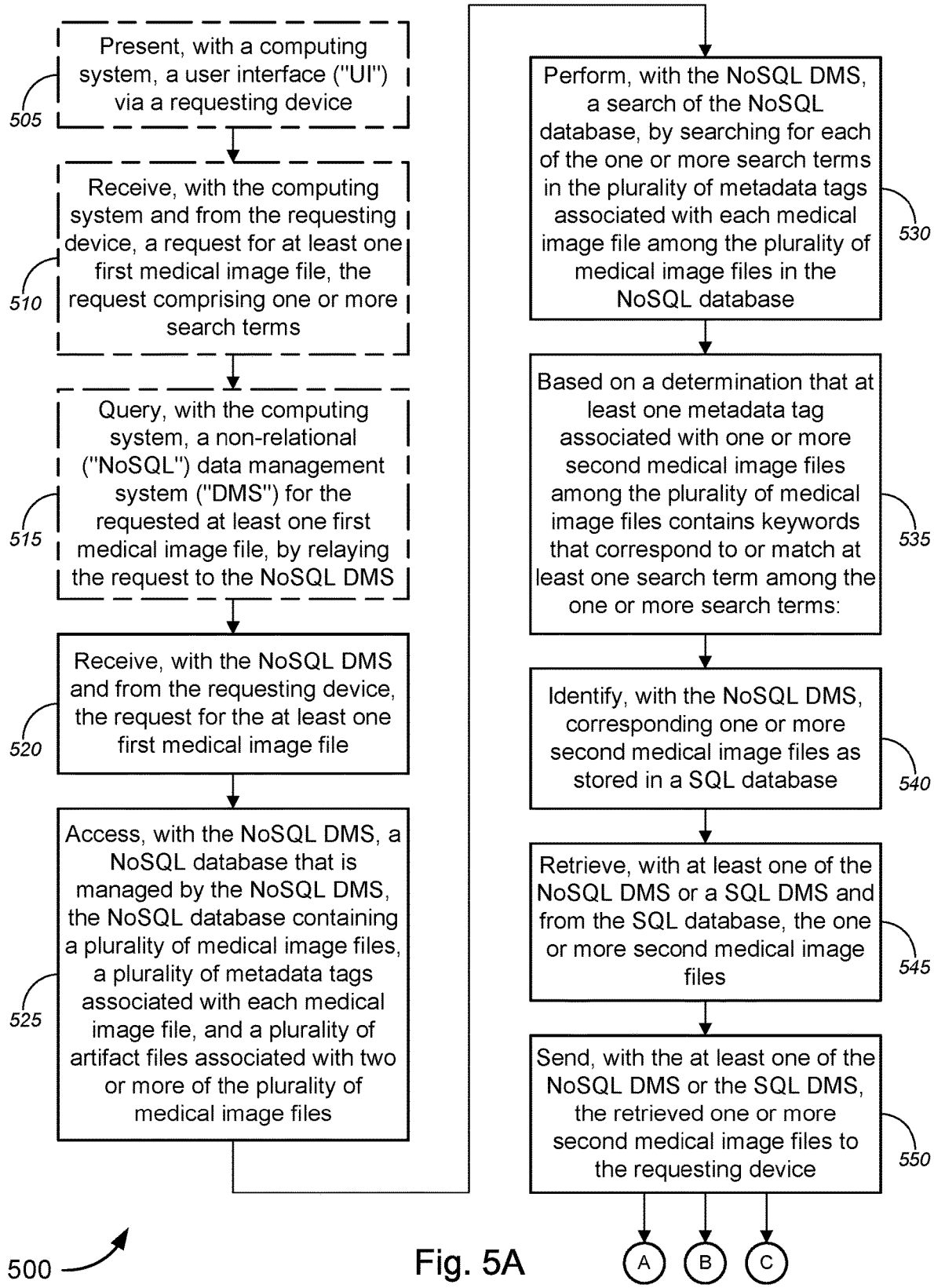

In the non-limiting embodiment of FIG. 5A, method 500, at optional block 505, may comprise presenting, with a computing system, a user interface ("UI") via a requesting device. Method 500 may further comprise receiving, with the computing system and from the requesting device, the request for the at least one first medical image file (optional block 510), the request comprising one or more search terms; and querying, with the computing system, a non-relational ("NoSQL") data management system ("DMS") for the requested at least one first medical image file, by relaying the request to the NoSQL DMS (optional block 515). In some cases, the request may be received via the UI.

According to some embodiments, the computing system may include, without limitation, at least one of a processor of a NoSQL DMS, a processor of a SQL DMS, a processor of a hybrid NoSQL/SQL DMS, a controller for both the NoSQL DMS and the SQL DMS, a server computer over a network, a cloud-based computing system over a network, or a distributed computing system, and/or the like. In some instances, the requesting device may include, but is not limited to, at least one of a laptop computer, a desktop computer, a tablet computer, a smart phone, a mobile phone, or a web client, and/or the like.

In some embodiments, the one or more search terms may include, without limitation, at least one of one or more search criteria, one or more keywords regarding at least one project description, one or more keywords regarding at least one source study name, one or more keywords regarding at least one anatomical region, one or more keywords regarding at least one characteristic of a class of patients, one or more keywords regarding at least one demographic of patients, one or more keywords regarding at least one physical characteristic of patients, one or more keywords regarding at least one characteristic of a disease, one or more keywords regarding at least one characteristic of one or more comorbidities, one or more keywords regarding at least one characteristic of each medical image that satisfies the one or more search criteria, one or more keywords regarding at least one characteristic of at least one modality used to obtain one or more medical images that satisfy the one or more search criteria, one or more keywords regarding at least one characteristic of at least one imaging device used to obtain one or more medical images that satisfy the one or more search criteria, or one or more keywords regarding at least one additional parameter, and/or the like.

Method 500 may comprise, at block 520, receiving, with the NoSQL DMS and from the requesting device (in some cases, via the computing system and/or via the UI), the request for the at least one first medical image file. At block 525, method 500 may comprise accessing, with the NoSQL DMS, a NoSQL database that is managed by the NoSQL DMS, the NoSQL database containing a plurality of medical image files, a plurality of metadata tags associated with each medical image file, and a plurality of artifact files associated with two or more of the plurality of medical image files, the NoSQL database containing mirrored copies of the plurality of medical image files that are stored in a relational ("SQL") database that is managed by a SQL DMS. In some embodiments, the plurality of medical image files contained in the NoSQL database and in the SQL database may each be organized in an image-centric hierarchy with image data being at a top level of the image-centric hierarchy and patient information associated with the image data being at a level below the top level of the image-centric hierarchy.

According to some embodiments, the plurality of artifact files may include, but is not limited to, at least one of one or more raw image data files, one or more document files, one or more image processing analysis files, one or more segmentation files, one or more three-dimensional ("3D") print files, one or more stereolithography ("STL") files, one or more measurement files, one or more experiment files, one or more project files, one or more machine algorithm files, or one or more report files, and/or the like. In some cases, the plurality of metadata tags may include, without limitation, flexible image tagging that is customizable to include one or more standard medical image metadata and one or more non-standard medical image metadata. In some instances, the one or more standard medical image metadata may include, but are not limited to, one or more digital imaging and communications in medicine ("DICOM")-compliant metadata, or the like. In some cases, the one or more non-standard medical image metadata may include, without limitation, at least one of contrast metadata, metadata associated with device attribute, metadata associated with implant technique, metadata regarding whether patient is healthy or not, metadata regarding quality of scan of image, metadata associated with one or more specific parameters used by at least one medical specialty, or one or more customizable metadata, and/or the like.

Method 500 may further comprise, at block 530, performing, with the NoSQL DMS, a search of the NoSQL database, by searching for each of the one or more search terms in the plurality of metadata tags associated with each medical image file among the plurality of medical image files in the NoSQL database. Method 500, at block 535, may comprise, based on a determination that at least one metadata tag associated with one or more second medical image files among the plurality of medical image files contains keywords that correspond to or match at least one search term among the one or more search terms: identifying, with the NoSQL DMS, corresponding one or more second medical image files as stored in the SQL database (block 540), wherein the search of the NoSQL database serves as an index search of the SQL database; retrieving, with at least one of the NoSQL DMS or the SQL DMS and from the SQL database, the one or more second medical image files (block 545); and sending, with the at least one of the NoSQL DMS or the SQL DMS, the retrieved one or more second medical image files to the requesting device (block 550). In some cases, sending the retrieved one or more second medical image files to the requesting device may comprise displaying the retrieved one or more second medical image files in the UI. Alternatively, or additionally, sending the retrieved one or more second medical image files to the requesting device may comprise sending, with the at least one of the NoSQL DMS or the SQL DMS, a list of relevant search results to the requesting device, the list of relevant search results comprising the retrieved one or more second medical image files, wherein the retrieved one or more second medical image files may include, without limitation, two or more medical image files that are associated with a plurality of different patients.

Method 500 might continue onto the process at block 555 in FIG. 5B following the circular marker denoted, "A," might continue onto the process at block 565 in FIG. 5C following the circular marker denoted, "B," might continue onto the process at block 570 in FIG. 5D following the circular marker denoted, "C."

At block 555 in FIG. 5B (following the circular marker denoted, "A"), method 500 may comprise converting, with the computing system, the retrieved one or more second medical image files into one or more DICOM-compliant search results. In some cases, displaying the retrieved one or more second medical image files in the UI may comprise displaying the retrieved one or more second medical image files as the converted one or more DICOM-compliant search results in the UI.

Method 500 may further comprise, based on a determination that a user's mouse cursor is hovering over a DICOM-compliant search result, generating and displaying, with the computing system, a pop-up display indicating specific information or values associated with the DICOM-compliant search result, based at least in part on the one or more search terms (block 560).

At block 565 in FIG. 5C (following the circular marker denoted, "B," from FIG. 5A), method 500 may comprise providing, with the computing system, one or more task options for each of the displayed retrieved one or more second medical image files in the UI. In some embodiments, the one or more task options may include, without limitation, at least one of options to download particular one or more third medical image files among the one or more second medical image files, options to add particular one or more fourth medical image files among the one or more second medical image files to at least one project group folder, options to link together at least two fifth medical image files among the one or more second medical image files, options to export one or more sixth medical image files among the one or more second medical image files, options to share one or more seventh medical image files among the one or more second medical image files, options to upload one or more eighth medical image files, options to start a new search, options to save a current search, options to manage saved searches, options to view recent searches, options to export searches, options to open a new project folder, options to save a current project folder, options to manage project folders, options to complete a current project, options to view active projects, or options to export project folders, and/or the like.

In some instances, two or more ninth medical image files among the one or more second medical image files that are obtained during a single imaging session may be grouped together as a single imaging asset with at least one of shared metadata, common metadata, or linked metadata, wherein the one or more task options may further comprise at least one of options to preview the two or more ninth medical image files together in the UI, options to download the two or more ninth medical image files as a single set of image files, options to export the two or more ninth medical image files as a single set of image files, options to share the two or more ninth medical image files as a single set of image files, or options to edit metadata associated with each of the two or more ninth medical image files individually or as a group, and/or the like. In some cases, the one or more task options may further comprise at least one of options to perform auto-segmentation for one or more tenth medical image files among the one or more second medical image files, or options to perform auto-measurements for one or more eleventh medical image files among the one or more second medical image files, and/or the like.

At block 570 in FIG. 5D (following the circular marker denoted, "C," from FIG. 5A), method 500 may comprise generating, with a model generation system, one or more three-dimensional ("3D") models based at least in part on at least one thirteenth medical image file among the retrieved one or more second medical image files.

Exemplary System and Hardware Implementation

Figure 6:
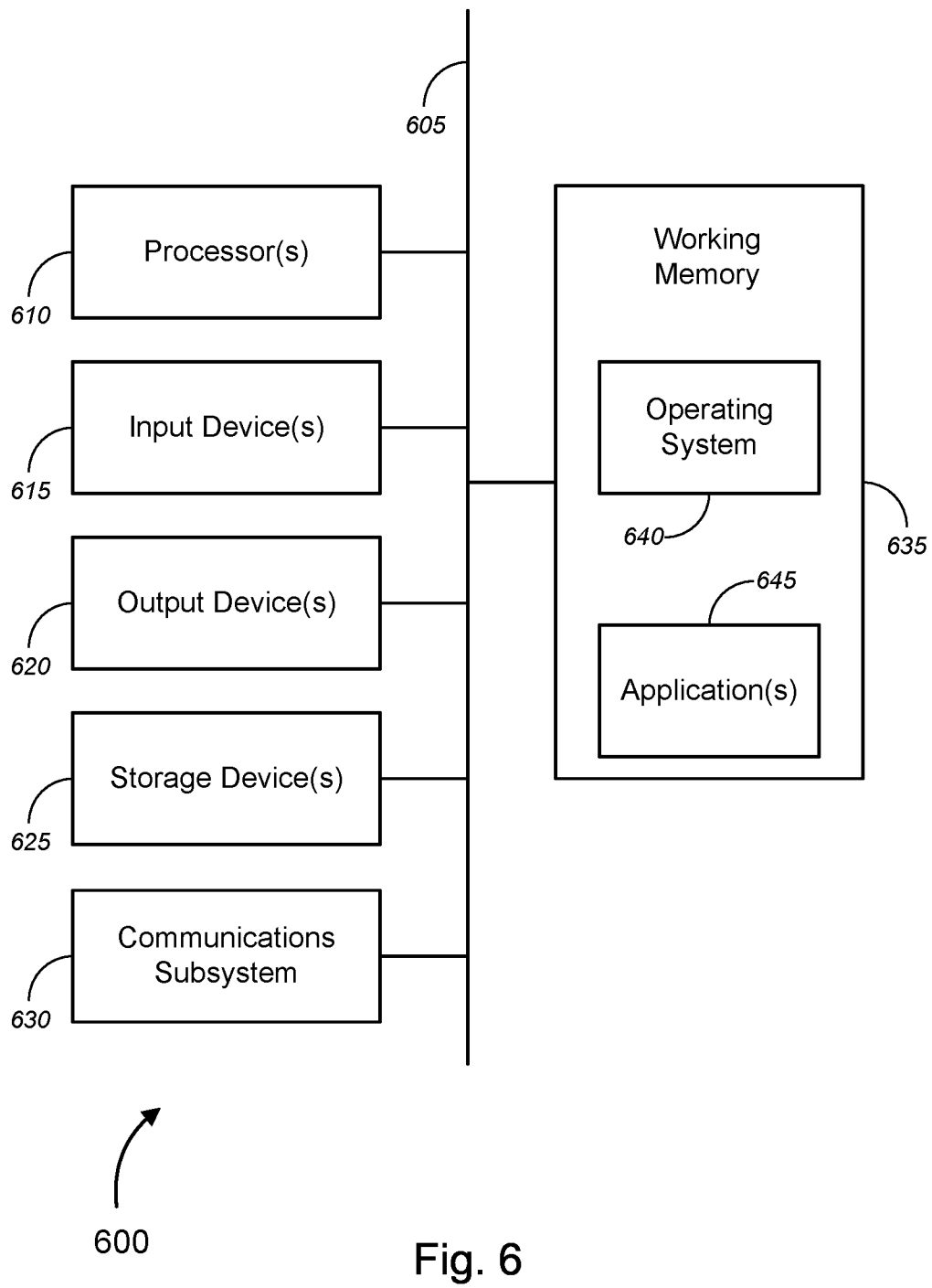
FIG. 6 is a block diagram illustrating an exemplary computer or system hardware architecture, in accordance with various embodiments.

FIG. 6 is a block diagram illustrating an exemplary computer or system hardware architecture, in accordance with various embodiments. FIG. 6 provides a schematic illustration of one embodiment of a computer system 600 of the service provider system hardware that can perform the methods provided by various other embodiments, as described herein, and/or can perform the functions of computer or hardware system (i.e., non-relational ("NoSQL") data management system ("DMS") 105, relational ("SQL") DMS 120, computing system 140, web servers 150 and 215, requesting devices 160a-160n and 220, imaging discover utility 205, and lightweight directory access protocol ("LDAP") provider system 270, etc.), as described above. It should be noted that FIG. 6 is meant only to provide a generalized illustration of various components, of which one or more (or none) of each may be utilized as appropriate. FIG. 6, therefore, broadly illustrates how individual system elements may be implemented in a relatively separated or relatively more integrated manner.

The computer or hardware system 600—which might represent an embodiment of the computer or hardware system (i.e., NoSQL DMS 105, SQL DMS 120, computing system 140, web servers 150 and 215, requesting devices 160a-160n and 220, imaging discover utility 205, and LDAP provider system 270, etc.), described above with respect to FIGS. 1-5—is shown comprising hardware elements that can be electrically coupled via a bus 605 (or may otherwise be in communication, as appropriate). The hardware elements may include one or more processors 610, including, without limitation, one or more general-purpose processors and/or one or more special-purpose processors (such as microprocessors, digital signal processing chips, graphics acceleration processors, and/or the like); one or more input devices 615, which can include, without limitation, a mouse, a keyboard, and/or the like; and one or more output devices 620, which can include, without limitation, a display device, a printer, and/or the like.

The computer or hardware system 600 may further include (and/or be in communication with) one or more storage devices 625, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable, and/or the like. Such storage devices may be configured to implement any appropriate data stores, including, without limitation, various file systems, database structures, and/or the like.

The computer or hardware system 600 might also include a communications subsystem 630, which can include, without limitation, a modem, a network card (wireless or wired), an infra-red communication device, a wireless communication device and/or chipset (such as a Bluetooth™ device, an 802.11 device, a WiFi device, a WiMax device, a WWAN device, cellular communication facilities, etc.), and/or the like. The communications subsystem 630 may permit data to be exchanged with a network (such as the network described below, to name one example), with other computer or hardware systems, and/or with any other devices described herein. In many embodiments, the computer or hardware system 600 will further comprise a working memory 635, which can include a RAM or ROM device, as described above.

The computer or hardware system 600 also may comprise software elements, shown as being currently located within the working memory 635, including an operating system 640, device drivers, executable libraries, and/or other code, such as one or more application programs 645, which may comprise computer programs provided by various embodiments (including, without limitation, hypervisors, VMs, and the like), and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 625 described above. In some cases, the storage medium might be incorporated within a computer system, such as the system 600. In other embodiments, the storage medium might be separate from a computer system (i.e., a removable medium, such as a compact disc, etc.), and/or provided in an installation package, such that the storage medium can be used to program, configure, and/or adapt a general purpose computer with the instructions/code stored thereon. These instructions might take the form of executable code, which is executable by the computer or hardware system 600 and/or might take the form of source and/or installable code, which, upon compilation and/or installation on the computer or hardware system 600 (e.g., using any of a variety of generally available compilers, installation programs, compression/decompression utilities, etc.) then takes the form of executable code.

It will be apparent to those skilled in the art that substantial variations may be made in accordance with specific requirements. For example, customized hardware (such as programmable logic controllers, field-programmable gate arrays, application-specific integrated circuits, and/or the like) might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer or hardware system (such as the computer or hardware system 600) to perform methods in accordance with various embodiments of the invention. According to a set of embodiments, some or all of the procedures of such methods are performed by the computer or hardware system 600 in response to processor 610 executing one or more sequences of one or more instructions (which might be incorporated into the operating system 640 and/or other code, such as an application program 645) contained in the working memory 635. Such instructions may be read into the working memory 635 from another computer readable medium, such as one or more of the storage device(s) 625. Merely by way of example, execution of the sequences of instructions contained in the working memory 635 might cause the processor(s) 610 to perform one or more procedures of the methods described herein.

The terms "machine readable medium" and "computer readable medium," as used herein, refer to any medium that participates in providing data that causes a machine to operate in a specific fashion. In an embodiment implemented using the computer or hardware system 600, various computer readable media might be involved in providing instructions/code to processor(s) 610 for execution and/or might be used to store and/or carry such instructions/code (e.g., as signals). In many implementations, a computer readable medium is a non-transitory, physical, and/or tangible storage medium. In some embodiments, a computer readable medium may take many forms, including, but not limited to, non-volatile media, volatile media, or the like. Non-volatile media includes, for example, optical and/or magnetic disks, such as the storage device(s) 625. Volatile media includes, without limitation, dynamic memory, such as the working memory 635. In some alternative embodiments, a computer readable medium may take the form of transmission media, which includes, without limitation, coaxial cables, copper wire, and fiber optics, including the wires that comprise the bus 605, as well as the various components of the communication subsystem 630 (and/or the media by which the communications subsystem 630 provides communication with other devices). In an alternative set of embodiments, transmission media can also take the form of waves (including without limitation radio, acoustic, and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Various forms of computer readable media may be involved in carrying one or more sequences of one or more instructions to the processor(s) 610 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer or hardware system 600. These signals, which might be in the form of electromagnetic signals, acoustic signals, optical signals, and/or the like, are all examples of carrier waves on which instructions can be encoded, in accordance with various embodiments of the invention.

The communications subsystem 630 (and/or components thereof) generally will receive the signals, and the bus 605 then might carry the signals (and/or the data, instructions, etc. carried by the signals) to the working memory 635, from which the processor(s) 605 retrieves and executes the instructions. The instructions received by the working memory 635 may optionally be stored on a storage device 625 either before or after execution by the processor(s) 610.

Figure 7:
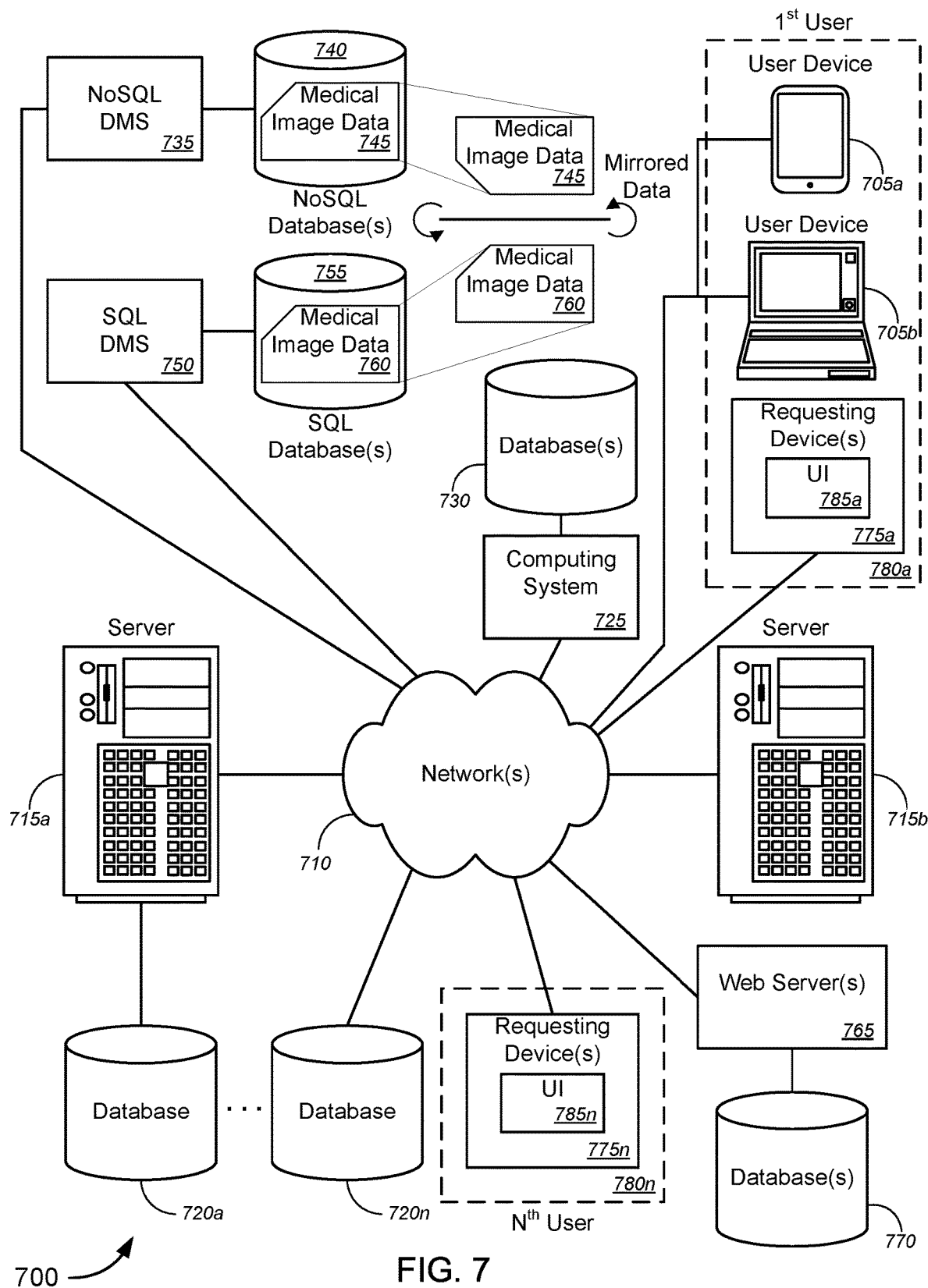
FIG. 7 is a block diagram illustrating a networked system of computers, computing systems, or system hardware architecture, which can be used in accordance with various embodiments.

As noted above, a set of embodiments comprises methods and systems for implementing image management, and, more particularly, to methods, systems, and apparatuses for implementing an imaging discovery utility for augmenting clinical image management. FIG. 7 illustrates a schematic diagram of a system 700 that can be used in accordance with one set of embodiments. The system 700 can include one or more user computers, user devices, or customer devices 705. A user computer, user device, or customer device 705 can be a general purpose personal computer (including, merely by way of example, desktop computers, tablet computers, laptop computers, handheld computers, and the like, running any appropriate operating system, several of which are available from vendors such as Apple, Microsoft Corp., and the like), cloud computing devices, a server(s), and/or a workstation computer(s) running any of a variety of commercially-available UNIX™ or UNIX-like operating systems. A user computer, user device, or customer device 705 can also have any of a variety of applications, including one or more applications configured to perform methods provided by various embodiments (as described above, for example), as well as one or more office applications, database client and/or server applications, and/or web browser applications. Alternatively, a user computer, user device, or customer device 705 can be any other electronic device, such as a thin-client computer, Internet-enabled mobile telephone, and/or personal digital assistant, capable of communicating via a network (e.g., the network(s) 710 described below) and/or of displaying and navigating web pages or other types of electronic documents. Although the exemplary system 700 is shown with two user computers, user devices, or customer devices 705, any number of user computers, user devices, or customer devices can be supported.

Certain embodiments operate in a networked environment, which can include a network(s) 710. The network(s) 710 can be any type of network familiar to those skilled in the art that can support data communications using any of a variety of commercially-available (and/or free or proprietary) protocols, including, without limitation, TCP/IP, SNA™, IPX™, AppleTalk™, and the like. Merely by way of example, the network(s) 710 (similar to network(s) 135 and/or 170 of FIG. 1, or the like) can each include a local area network ("LAN"), including, without limitation, a fiber network, an Ethernet network, a Token-Ring™ network, and/or the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including, without limitation, a network operating under any of the IEEE 802.11 suite of protocols, the Bluetooth™ protocol known in the art, and/or any other wireless protocol; and/or any combination of these and/or other networks. In a particular embodiment, the network might include an access network of the service provider (e.g., an Internet service provider ("ISP")). In another embodiment, the network might include a core network of the service provider, and/or the Internet.

Embodiments can also include one or more server computers 715. Each of the server computers 715 may be configured with an operating system, including, without limitation, any of those discussed above, as well as any commercially (or freely) available server operating systems. Each of the servers 715 may also be running one or more applications, which can be configured to provide services to one or more clients 705 and/or other servers 715.

Merely by way of example, one of the servers 715 might be a data server, a web server, a cloud computing device(s), or the like, as described above. The data server might include (or be in communication with) a web server, which can be used, merely by way of example, to process requests for web pages or other electronic documents from user computers 705. The web server can also run a variety of server applications, including HTTP servers, FTP servers, CGI servers, database servers, Java servers, and the like. In some embodiments of the invention, the web server may be configured to serve web pages that can be operated within a web browser on one or more of the user computers 705 to perform methods of the invention.

The server computers 715, in some embodiments, might include one or more application servers, which can be configured with one or more applications accessible by a client running on one or more of the client computers 705 and/or other servers 715. Merely by way of example, the server(s) 715 can be one or more general purpose computers capable of executing programs or scripts in response to the user computers 705 and/or other servers 715, including, without limitation, web applications (which might, in some cases, be configured to perform methods provided by various embodiments). Merely by way of example, a web application can be implemented as one or more scripts or programs written in any suitable programming language, such as Java™, C, C#™ or C++, and/or any scripting language, such as Perl, Python, or TCL, as well as combinations of any programming and/or scripting languages. The application server(s) can also include database servers, including, without limitation, those commercially available from Oracle™, Microsoft™, Sybase™, IBM™, and the like, which can process requests from clients (including, depending on the configuration, dedicated database clients, API clients, web browsers, etc.) running on a user computer, user device, or customer device 705 and/or another server 715. In some embodiments, an application server can perform one or more of the processes for implementing image management, and, more particularly, to methods, systems, and apparatuses for implementing an imaging discovery utility for augmenting clinical image management, as described in detail above. Data provided by an application server may be formatted as one or more web pages (comprising HTML, JavaScript, etc., for example) and/or may be forwarded to a user computer 705 via a web server (as described above, for example). Similarly, a web server might receive web page requests and/or input data from a user computer 705 and/or forward the web page requests and/or input data to an application server. In some cases, a web server may be integrated with an application server.

In accordance with further embodiments, one or more servers 715 can function as a file server and/or can include one or more of the files (e.g., application code, data files, etc.) necessary to implement various disclosed methods, incorporated by an application running on a user computer 705 and/or another server 715. Alternatively, as those skilled in the art will appreciate, a file server can include all necessary files, allowing such an application to be invoked remotely by a user computer, user device, or customer device 705 and/or server 715.

It should be noted that the functions described with respect to various servers herein (e.g., application server, database server, web server, file server, etc.) can be performed by a single server and/or a plurality of specialized servers, depending on implementation-specific needs and parameters.

In certain embodiments, the system can include one or more databases 720a-720n (collectively, "databases 720"). The location of each of the databases 720 is discretionary: merely by way of example, a database 720a might reside on a storage medium local to (and/or resident in) a server 715a (and/or a user computer, user device, or customer device 705). Alternatively, a database 720n can be remote from any or all of the computers 705, 715, so long as it can be in communication (e.g., via the network 710) with one or more of these. In a particular set of embodiments, a database 720 can reside in a storage-area network ("SAN") familiar to those skilled in the art. (Likewise, any necessary files for performing the functions attributed to the computers 705, 715 can be stored locally on the respective computer and/or remotely, as appropriate.) In one set of embodiments, the database 720 can be a relational database, such as an Oracle database, that is adapted to store, update, and retrieve data in response to SQL-formatted commands. The database might be controlled and/or maintained by a database server, as described above, for example.

According to some embodiments, system 700 might further comprise computing system 725 and corresponding database(s) 730 (similar to computing system 140 and corresponding database(s) 145 in FIG. 1, or the like), a non-relational ("NoSQL") data management system ("DMS") 735 and corresponding NoSQL database 740 (similar to NoSQL DMS 105 and corresponding database(s) 110 in FIG. 1, or the like). In some embodiments, the NoSQL database 740 may contain medical image data 745, which may include, without limitation, a plurality of medical image files, a plurality of metadata tags associated with each medical image file, and a plurality of artifact files associated with two or more of the plurality of medical image files, and/or the like. System 700 may further comprise a relational ("SQL") DMS 750 and corresponding SQL database 755 (similar to SQL DMS 120 and corresponding database(s) 125 in FIG. 1, or the like). According to some embodiments, the SQL database 755 may contain medical image data 760, which may include, without limitation, a plurality of medical image files, a plurality of metadata tags associated with each medical image file, and a plurality of artifact files associated with two or more of the plurality of medical image files, and/or the like. In some instances, the NoSQL database 740 may contain mirrored copies of the plurality of medical image files that are stored in the SQL database 755 that is managed by the SQL DMS 750 (denoted in FIG. 7 by symbols labelled "Mirrored Data"). The plurality of medical image files contained in the NoSQL database 740 and in the SQL database 755 may each be organized in an image-centric hierarchy with image data being at a top level of the image-centric hierarchy and patient information associated with the image data being at a level below the top level of the image-centric hierarchy, which is an improvement in terms of image discover and management over conventional data management systems, which are patient-centric, with the patient information being at a top level of the patient-centric hierarchy and image information associated with the patient data being at a level below the top level of the patient-centric hierarchy. In some instances, the computing system 725 may include, but is not limited to, at least one of a processor of a NoSQL DMS, a processor of a SQL DMS, a processor of a hybrid NoSQL/SQL DMS, a controller for both the NoSQL DMS and the SQL DMS, a server computer over a network, a cloud-based computing system over a network, or a distributed computing system, and/or the like.

In some cases, the plurality of artifact files may include, but is not limited to, at least one of one or more raw image data files, one or more document files, one or more image processing analysis files, one or more segmentation files, one or more three-dimensional ("3D") print files, one or more stereolithography ("STL") files, one or more measurement files, one or more experiment files, one or more project files, one or more machine algorithm files, or one or more report files, and/or the like. In some instances, the plurality of metadata tags may include, without limitation, flexible image tagging that is customizable to include one or more standard medical image metadata and one or more non-standard medical image metadata. In some cases, the one or more standard medical image metadata may comprise one or more digital imaging and communications in medicine ("DICOM")-compliant metadata. In some instances, the one or more non-standard medical image metadata may include, but are not limited to, at least one of contrast metadata, metadata associated with device attribute, metadata associated with implant technique, metadata regarding whether patient is healthy or not, metadata regarding quality of scan of image, metadata associated with one or more specific parameters used by at least one medical specialty, or one or more customizable metadata, and/or the like.

System 700 may further comprise web server(s) 765 and corresponding database(s) 770 (similar to web server(s) 150 and corresponding database(s) 155 in FIG. 1, or the like). System 700 may further comprise one or more requesting devices 775a-775n (collectively, "requesting devices 775" or the like; similar to requesting devices 160a-160n in FIG. 1, or the like) associated with first through $N^{th}$ users 780a-780n (collectively, "users 780" or the like; similar to users 165a-165n in FIG. 1, or the like), respectively. In some instances, the one or more requesting devices may each include, but is not limited to, at least one of a laptop computer, a desktop computer, a tablet computer, a smart phone, a mobile phone, or a web client, and/or the like. System 700 may further comprise one or more user interfaces ("UIs") 785a-785n (collectively, "UIs 785" or the like; similar to UIs 175a-175n in FIG. 1, or the like), each being displayed in a corresponding requesting device 775 among the one or more requesting devices 775a-775n or in user device 705a or 705b, or the like.

In operation, the NoSQL DMS 735 might receive, from a requesting device 775 that is associated with a user 780 (via network(s) 710, or the like), a request for at least one first medical image file, the request comprising one or more search terms. In some embodiments, the one or more search terms may include, without limitation, at least one of one or more search criteria, one or more keywords regarding at least one project description, one or more keywords regarding at least one source study name, one or more keywords regarding at least one anatomical region, one or more keywords regarding at least one characteristic of a class of patients, one or more keywords regarding at least one demographic of patients, one or more keywords regarding at least one physical characteristic of patients, one or more keywords regarding at least one characteristic of a disease, one or more keywords regarding at least one characteristic of one or more comorbidities, one or more keywords regarding at least one characteristic of each medical image that satisfies the one or more search criteria, one or more keywords regarding at least one characteristic of at least one modality used to obtain one or more medical images that satisfy the one or more search criteria, one or more keywords regarding at least one characteristic of at least one imaging device used to obtain one or more medical images that satisfy the one or more search criteria, or one or more keywords regarding at least one additional parameter, and/or the like.

The NoSQL DMS 735 might access NoSQL database(s) 740 that is managed by the NoSQL DMS 735, and might perform a search of the NoSQL database(s) 740, by searching for each of the one or more search terms in the plurality of metadata tags associated with each medical image file among the plurality of medical image files (i.e., medical image data 745, or the like) in the NoSQL database(s) 740. Based on a determination that at least one metadata tag associated with one or more second medical image files among the plurality of medical image files contains keywords that correspond to or match at least one search term among the one or more search terms, the NoSQL DMS 735 might identify corresponding one or more second medical image files (i.e., medical image data 760, or the like) as stored in the SQL database(s) 755, where the search of the NoSQL database(s) 740 serves as an index search of the SQL database(s) 755—due to the mirrored data 745 and 760 stored in the NoSQL and SQL databases 740 and 755. At least one of the NoSQL DMS 735 and/or the SQL DMS 750 might retrieve, from the SQL database(s) 755, the one or more second medical image files, and might send the retrieved one or more second medical image files to the requesting device 775. In some instances, sending the retrieved one or more second medical image files to the requesting device may comprise sending, with the at least one of the NoSQL DMS 735 or the SQL DMS 750, a list of relevant search results to the requesting device, the list of relevant search results comprising the retrieved one or more second medical image files, wherein the retrieved one or more second medical image files may include, but is not limited to, two or more medical image files that are associated with a plurality of different patients.

In some embodiments, computing system 725 and/or web server(s) 765 (collectively, "computing system" or the like) might receive, from the requesting device 775, the request for the at least one first medical image file, and might query the NoSQL DMS 735 for the requested at least one first medical image file, by relaying the request to the NoSQL DMS 735. In some cases, the computing system might present the UI 785 via the requesting device 775. In such cases, the request might be received via the UI 785. In some instances, sending the retrieved one or more second medical image files to the requesting device may comprise displaying the retrieved one or more second medical image files in the UI 785.

According to some embodiments, the computing system might convert the retrieved one or more second medical image files into one or more DICOM-compliant search results. In some cases, displaying the retrieved one or more second medical image files in the UI 785 may comprise displaying the retrieved one or more second medical image files as the converted one or more DICOM-compliant search results in the UI 785. In some instances, based on a determination that a user's mouse cursor is hovering over a DICOM-compliant search result, the computing system might generate and display a pop-up display indicating specific information or values associated with the DICOM-compliant search result, based at least in part on the one or more search terms.

In some embodiments, the computing system might provide one or more task options for each of the displayed retrieved one or more second medical image files in the UI 785. In some cases, the one or more task options may include, without limitation, at least one of options to download particular one or more third medical image files among the one or more second medical image files, options to add particular one or more fourth medical image files among the one or more second medical image files to at least one project group folder, options to link together at least two fifth medical image files among the one or more second medical image files, options to export one or more sixth medical image files among the one or more second medical image files, options to share one or more seventh medical image files among the one or more second medical image files, options to upload one or more eighth medical image files, options to start a new search, options to save a current search, options to manage saved searches, options to view recent searches, options to export searches, options to open a new project folder, options to save a current project folder, options to manage project folders, options to complete a current project, options to view active projects, or options to export project folders, and/or the like.

These and other functions of the system 700 (and its components) are described in greater detail above with respect to FIGS. 1-5.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A method, comprising:
   determining that contents of one of a non-relational ("NoSQL") database, via a NoSQL data management system ("DMS"), or a relational ("SQL") database, via a SQL DMS, have changed;
   autonomously mirroring the changed contents in the other of the NoSQL database or the SQL database, via the respective DMS, based on the determination, the NoSQL database containing a plurality of medical image files, a plurality of metadata tags associated with each medical image file, and a plurality of artifact files associated with two or more of the plurality of medical image files, the NoSQL database containing mirrored copies of the plurality of medical image files that are stored in the SQL database, wherein the plurality of medical image files contained in the NoSQL database and in the SQL database are each organized in an image-centric hierarchy with image data being at a top level of the image-centric hierarchy and patient information associated with the image data being at a level below the top level of the image-centric hierarchy;
   receiving, with the NoSQL DMS and from a requesting device, a request for the plurality of medical image files, the request comprising one or more search terms;
   based on a determination that at least one metadata tag associated with the plurality of medical image files contains keywords that correspond to or match at least one search term among the one or more search terms:
      identifying, with the NoSQL DMS, corresponding medical image files of the plurality of medical image files as stored in the SQL database;
      retrieving, with at least one of the NoSQL DMS or the SQL DMS and from the SQL database, the plurality of medical image files; and
      sending, with the at least one of the NoSQL DMS or the SQL DMS, the retrieved plurality of medical image files to the requesting device.

2. The method of claim 1, further comprising:
   receiving, with the NoSQL DMS and from the requesting device, a request for at least one first medical image file, the request comprising one or more search terms;
   accessing, with the NoSQL DMS, the NoSQL database that is managed by the NoSQL DMS; and
   performing, with the NoSQL DMS, a search of the NoSQL database, by searching for each of the one or more search terms in the plurality of metadata tags associated with each medical image file among the plurality of medical image files in the NoSQL database.

3. The method of claim 2, further comprising:
   wherein identifying further includes identifying, with the NoSQL DMS, corresponding one or more second medical image files as stored in the SQL database, wherein the search of the NoSQL database serves as an index search of the SQL database;
   wherein retrieving further includes retrieving, with at least one of the NoSQL DMS or the SQL DMS and from the SQL database, the one or more second medical image files; and
   wherein sending further includes sending, with the at least one of the NoSQL DMS or the SQL DMS, the retrieved one or more second medical image files to the requesting device.

4. The method of claim 2, wherein the requesting device comprises at least one of a laptop computer, a desktop computer, a tablet computer, a smart phone, a mobile phone, or a web client.

5. The method of claim 3, further comprising:
   receiving, with a computing system and from the requesting device, the request for the at least one first medical image file; and
   querying, with the computing system, the NoSQL DMS for the requested at least one first medical image file, by relaying the request to the NoSQL DMS.

6. The method of claim 3, further comprising:
   generating, with a model generation system, one or more three-dimensional ("3D") models based on at least one thirteenth medical image file among the retrieved one or more second medical image files.

7. The method of claim 1, wherein the plurality of metadata tags comprises flexible image tagging that is customizable to include one or more first medical image metadata and one or more second medical image metadata.

8. The method of claim 7, wherein the one or more first medical image metadata comprise one or more digital imaging and communications in medicine ("DICOM")-compliant metadata.

9. The method of claim 1, further comprising:
   receiving, with the NoSQL DMS and from a requesting device, a request to modify a metadata tag associated with a medical image file that is stored and mirrored in each of the NoSQL database and the SQL database; and
   presenting, via one of the NoSQL DMS or the SQL DMS, a user interface ("UI") with options for dynamically modifying metadata tags associated with the medical image file.

10. The method of claim 9, wherein the options to dynamically modify metadata tags includes at least one selected from the group consisting of dynamically adding group specific metadata tags to metadata fields of the medical image file, dynamically modifying group specific metadata tags in metadata fields of the medical image file, dynamically deleting group specific metadata tags in metadata fields of the medical image file, dynamically defining new group specific metadata fields of the medical image file, dynamically modifying group specific metadata fields of the medical image file, dynamically deleting group specific metadata fields of the medical image file, and dynamically linking a metadata field with one or more artifact files.

11. A method, comprising:
   accessing, with a non-relational ("NoSQL") data management system ("DMS"), a NoSQL database that is managed by the NoSQL DMS, the NoSQL database containing a plurality of medical image files, a plurality of metadata tags associated with each medical image file, and a plurality of artifact files associated with two or more of the plurality of medical image files, the NoSQL database containing mirrored copies of the plurality of medical image files that are stored in a relational ("SQL") database that is managed by a SQL DMS;
   performing, with the NoSQL DMS, a search of the NoSQL database, by searching for each of one or more search terms in the plurality of metadata tags associated with each medical image file among the plurality of medical image files in the NoSQL database; and
   based on a determination that at least one metadata tag associated with one or more second medical image files among the plurality of medical image files contains keywords that correspond to or match at least one search term among the one or more search terms:
- identifying, with the NoSQL DMS, corresponding one or more second medical image files as stored in the SQL database, wherein the search of the NoSQL database serves as an index search of the SQL database;
- retrieving, with at least one of the NoSQL DMS or the SQL DMS and from the SQL database, the one or more second medical image files; and
- sending, with the at least one of the NoSQL DMS or the SQL DMS, the retrieved one or more second medical image files to a requesting device.

12. The method of claim 11, further comprising:
- receiving, with a computing system and from a requesting device, a request for at least one first medical image file; and
- querying, with the computing system, the NoSQL DMS for the requested at least one first medical image file, by relaying the request to the NoSQL DMS.

13. The method of claim 12, further comprising:
- presenting, with the computing system, a user interface ("UI") via the requesting device;
  - wherein the request is received via the UI; and
  - wherein sending the retrieved one or more second medical image files to the requesting device includes displaying the retrieved one or more second medical image files in the UI.

14. The method of claim 13, further comprising:
- converting, with the computing system, the retrieved one or more second medical image files into one or more digital imaging and communications in medicine ("DICOM")-compliant search results;
  - wherein displaying the retrieved one or more second medical image files in the UI includes displaying the retrieved one or more second medical image files as the converted one or more DICOM-compliant search results in the UI.

15. The method of claim 14, further comprising:
- based on a determination that a user's mouse cursor is hovering over a DICOM-compliant search result, generating and displaying, with the computing system, a pop-up display indicating specific information or values associated with the DICOM-compliant search result, based at least in part on the one or more search terms.

16. The method of claim 13, further comprising:
- providing, with the computing system, one or more task options for each of the displayed retrieved one or more second medical image files in the UI;
  - wherein the one or more task options includes at least one selected from the group consisting of options to download particular one or more third medical image files among the one or more second medical image files, options to add particular one or more fourth medical image files among the one or more second medical image files to at least one project group folder, options to link together at least two fifth medical image files among the one or more second medical image files, options to export one or more sixth medical image files among the one or more second medical image files, options to share one or more seventh medical image files among the one or more second medical image files, options to upload one or more eighth medical image files, options to start a new search, options to save a current search, options to manage saved searches, options to view recent searches, options to export searches, options to open a new project folder, options to save a current project folder, options to manage project folders, options to complete a current project, options to view active projects, and options to export project folders.

17. The method of claim 16, wherein two or more ninth medical image files among the one or more second medical image files that are obtained during a single imaging session are grouped together as a single imaging asset with at least one of shared metadata, common metadata, or linked metadata, wherein the one or more task options further includes at least one selected from the group consisting of options to preview the two or more ninth medical image files together in the UI, options to download the two or more ninth medical image files as a single set of image files, options to export the two or more ninth medical image files as a single set of image files, options to share the two or more ninth medical image files as a single set of image files, and options to edit metadata associated with each of the two or more ninth medical image files individually or as a group.

18. The method of claim 16, wherein the one or more task options further includes at least one selected from the group consisting of options to perform auto-segmentation for one or more tenth medical image files among the one or more second medical image files and options to perform auto-measurements for one or more eleventh medical image files among the one or more second medical image files.

19. The method of claim 12, wherein the computing system includes at least one selected from the group consisting of a processor of a NoSQL DMS, a processor of a SQL DMS, a processor of a hybrid NoSQL/SQL DMS, a controller for both the NoSQL DMS and the SQL DMS, a server computer over a network, a cloud-based computing system over a network, and a distributed computing system.

20. The method of claim 11, further comprising:
- generating, with a model generation system, one or more three-dimensional ("3D") models based on at least one thirteenth medical image file among the retrieved one or more second medical image files.

* * * * *